(12) United States Patent
Ho et al.

(10) Patent No.: US 7,811,558 B2
(45) Date of Patent: Oct. 12, 2010

(54) USE OF STABILIZED PLATELETS AS HEMOSTATIC AGENT

(75) Inventors: David Ho, Fairfax, VA (US); Cindy S. Orser, McLean, VA (US); Alan S. Rudolph, Potomac, MD (US)

(73) Assignee: Cellphire, Inc., Rockville, MD (US)

( * ) Notice: Subject to any disclaimer, the term of this patent is extended or adjusted under 35 U.S.C. 154(b) by 271 days.

(21) Appl. No.: 11/202,376

(22) Filed: Aug. 12, 2005

(65) Prior Publication Data

US 2006/0034809 A1  Feb. 16, 2006

Related U.S. Application Data

(60) Provisional application No. 60/600,838, filed on Aug. 12, 2004, provisional application No. 60/619,930, filed on Oct. 20, 2004.

(51) Int. Cl.
*A01N 65/00* (2009.01)

(52) U.S. Cl. .................................. 424/93.72

(58) Field of Classification Search ........................ None
See application file for complete search history.

(56) References Cited

U.S. PATENT DOCUMENTS

| | | | |
|---|---|---|---|
| 5,736,313 A | 4/1998 | Spargo et al. | |
| 5,993,804 A * | 11/1999 | Read et al. | 424/93.72 |
| 6,221,575 B1 | 4/2001 | Roser et al. | |
| 7,169,606 B2 | 1/2007 | DePablo et al. | |

| | | | |
|---|---|---|---|
| 2003/0022333 A1 | 1/2003 | Bronshtein | |
| 2005/0074402 A1 | 4/2005 | Cagnolini et al. | |

FOREIGN PATENT DOCUMENTS

| | | |
|---|---|---|
| WO | WO 01/58266 | 8/2001 |
| WO | WO 2004/050896 | 6/2004 |

OTHER PUBLICATIONS

Dictionary definition of "expose", http://dictionary.reference.com/browse/expose, accessed Jul. 18, 2009.*
Strong, D.M., Transfusion Medicine Bulletin, Vo. 2, No. 2, Jul. 1999.
Wolkers, W.F. et al., "Human Platelets Loaded with Trehalose Survive Freeze-Drying", *Cryobiology* 42:79-87, 2001.
International Search Report, PCT/US05/28559, Apr. 2007.
Decision to Grant, European Patent Application No. EP 05 78 4165; Dec. 2009.
Office Action, Chinese Patent Application No. 2005800348733, Feb. 2009.
Decision to Grant, Chinese Patent Application No. 2005800348733, Jan. 2010.
Examination Report, New Zealand Patent Application No. 553389, Jul. 2008.
Notice of Acceptance, New Zealand Patent Application No. 553389, Oct. 2009.

* cited by examiner

*Primary Examiner*—Sandra Saucier
(74) *Attorney, Agent, or Firm*—MHZ Technology Law Group

(57) ABSTRACT

The present invention provides compositions comprising freeze-dried platelets, microparticles, or both for use as a hemostat, such as for treating bleeding or injuries associated with bleeding. It also provides methods of treating injuries or wounds, and methods of causing blood to clot. Likewise, it provides methods of promoting healing of wounds or of healing wounds.

13 Claims, 11 Drawing Sheets

USE OF STABILIZED PLATELETS AS HEMOSTATIC AGENT

CROSS-REFERENCE TO RELATED APPLICATIONS

This application relies on and claims the benefit of the filing date of U.S. provisional application 60/600,838, filed 12 Aug. 2004; U.S. provisional application 60/619,930, filed 20 Oct. 2004; U.S. application Ser. No. 11/152,774, filed 15 Jun. 2005; and U.S. application Ser. No. 11/197,310, filed 5 Aug. 2005, the entire disclosures of all of which are hereby incorporated by reference.

STATEMENT OF GOVERNMENT INTEREST

This invention was made partially with U.S. Government support from the United States Department of Defense Advanced Research Projects Agency (DARPA) through the Department of the Navy (SPAWAR) under Contract No. N6600103C8031. The U.S. Government has certain rights in the invention.

BACKGROUND OF THE INVENTION

1. Field of the Invention

The present invention relates to the field of dry platelet preparations. More specifically, the present invention relates to dry platelet preparations and their use in tissue regeneration and as a hemostat for clotting of wounds.

2. Description of Related Art

Platelets are formed in the bone marrow as fragments of megakaryocytes. They are irregularly-shaped, colorless bodies that are present in blood at a concentration of 150,000-450,000 per microliter (ul). Platelets play a crucial role in hemostasis, and they are the first line of defense against blood escaping from injured blood vessels. When bleeding from a wound suddenly occurs, the platelets gather at the wound and attempt to block the blood flow by forming a clot. There are two general mechanisms to clot formation. In one mechanism, a clot begins to form when the blood is exposed to air. The platelets sense the presence of air and react with fibrinogen to begin forming fibrin. The resulting fibrin forms a web-like mesh that traps blood cells within it. In the other general mechanism, damaged blood vessels release a chemical signal that increases the stickiness of platelets in the area of the injury. The sticky platelets adhere to the damaged area and gradually form a platelet plug. At the same time, the platelets release a series of chemical signals that prompt other factors in the blood to reinforce the platelet plug. Between the platelet and its reinforcements, a sturdy clot is created that acts as a patch while the damaged area heals.

Platelets, in the form of platelet gels, have been used extensively to accelerate wound healing and, in conjunction with autologous fibrin glue, autologous platelet gel has been shown to improve perioperative hemostasis and reduce blood transfusion needs in surgery to replace the ascending aorta (Christenson and Kalangos, 2004). Costasis Surgical Hemostat (Costatis®). A combination of bovine thrombin, bovine collagen, and plasma as the source of fibrinogen and platelets has been shown to work well in the in vivo bleeding rabbit kidney and spleen model (Prior et al., 1999). Nevertheless, other studies have shown that platelet gel, when used alone, is not an effective hemostasis agent (Wajon et al., 2001). Despite of the contradicting findings regarding platelets and their role as hemostasis agents, there is little doubt about the pro-coagulant nature of platelet microparticles; these essential components, often overlooked, are increasingly being recognized as active participants in the in vitro and in vivo clotting process (Nieuwland et al., 1997). When platelets are stimulated with a combination of physiological agonists, such as thrombin and collagen, they release large quantities of microparticles (Sims et al., 1988; Tans et al., 1991). The activated platelets and microparticles express an aminophospholipid, which provides a procoagulant surface to support the formation of activated clotting enzymes in the intrinsic, extrinsic, and common pathways (Rosing et al., 1985).

Compared with activated platelets, microparticles contain a higher density of high-affinity binding sites for activated factor IX (IXa) (Hoffman et al., 1992) and factor Va (Sims et al., 1988). They have a continuous expression of high-affinity binding sites for factor VIII (Gilbert et al., 1991) and support both factor Xa activity (Gilbert et al., 1991; Holme et al., 1995) and prothrombinase activity (Sims et al., 1989).

Aside from the fact that platelet microparticles are important components in the hemostatic response, platelets, in the form of platelet gels, have been used in surgical wound healing applications as well as to treat difficult to heal wounds (Mazzucco et al., 2004). Moreover, the use of platelets in the form of platelet rich plasma has expanded into novel applications, such as bio-tissue engineering or autologous and allogenic tissue grafts, as well as osseous bone integration and soft tissue regeneration (Oikarinen et al., 2003). This is because platelets contain a number of important growth factors within their alpha granules that contribute to the process of hemostasis and wound healing. Studies have found that growth factors, such as platelet derived wound healing factors (PDWHF), platelet-derived growth factor (PDGF), transforming growth factor (TGF), and insulin growth factors (IGF), among others, are important in different stages of the wound-healing cascade and greatly influence mitogenic and cellular differentiation activities (Pierce et al., 1989; Steed, 1997).

These findings have lead to the development of strategies for growth factor replacement. For example, Regranex®, a recombinant human PDGF in a carrier gel, is used to treat diabetic wounds, while others, such as TGF, are currently being tested for FDA approval. Nevertheless, a single growth factor applied into a wound is not as effective as multiple growth factors. This is not surprising since wound healing is a complex integration of cascades that requires multiple growth factors for different stimulatory and inhibitory functions at different phases within the process.

Even though numerous advances in blood products and wound healing have taken place over the last several years, there is still a need for improved compositions for treating wounds, such as by hemostasis or clotting of wounds. Likewise, there is a need for methods of treating wounds to stop blood loss that are rapid, effective, and suitable for use in multiple settings.

SUMMARY OF THE INVENTION

The current invention addresses the needs in the art by providing compositions that can be used as hemostats, to form clots at sites of injury involving bleeding, and to promote tissue regeneration and healing. The compositions can be produced following the methods provided herein, and typically contain platelets, microparticles, such as platelet-derived microparticles, or both. Accordingly, the present invention provides methods of making hemostats and methods of using the hemostats, such as for treating wounds and bleeding. Kits are provided to contain the compositions.

In a first aspect, the invention provides freeze-dried platelets and compositions comprising freeze-dried platelets. The freeze-dried platelets can be used as an injectable or infusible substance for treatment of bleeding in a patient, or can be used as a direct treatment for bleeding that is accessible from outside the body. The likewise can be used for diagnostic purposes or for in vitro studies, such as for studies on the blood clotting process. The freeze-dried platelets, or rehydrated platelets made from them, can have properties of freshly obtained or in-dated platelets sufficient to provide clotting functions, and promote wound healing.

In another aspect, the invention provides methods of making freeze-dried platelets. The method generally comprises obtaining platelets, exposing the platelets to at least one saccharide under conditions that are sufficient for the saccharide to be taken into the platelets; adding a cryoprotectant; and lyophilizing. The freeze-dried platelets can be re-constituted or re-hydrated (used interchangeably herein) by exposure to an aqueous liquid, such as water or an aqueous buffer. Alternatively, the freeze-dried platelet preparations can be used directly in treating a subject suffering from a bleeding wound or a bleeding disorder.

In an additional aspect, the present invention provides methods of treating a subject in need of platelets. In general, the methods comprise obtaining freeze-dried platelets, and administering them to a subject in need of platelets. The methods can comprise the optional step of rehydrating the platelets prior to administering them to the subject. The subject can be any subject in need, such as one that is suffering from a bleeding wound or one who has a bleeding disease or disorder.

In another aspect, the present invention provides methods of using the freeze-dried platelets (or reconstituted platelets derived therefrom) for diagnostic or research purposes. The methods of diagnosis are typically performed in vitro, but may be performed in vivo on test animals if desired. The methods of diagnosis generally are performed to identify bleeding disorders and causes of those disorders. Research methods generally relate to discovery of causes of bleeding disorders, such as the molecular basis for a particular person's inability to normally control bleeding in response to wounds or other injuries. The research methods can also relate to study of the effects of drug treatments on the blood clotting system of individuals (e.g., side effects that negatively affect blood clotting).

In yet another aspect, the invention provides kits. In general, a kit of the invention comprises the freeze-dried platelets of the invention. The kit can be configured to supply the freeze-dried platelets for use in in vivo treatments, for use in in vitro diagnostics, or for use in in vitro or in vivo research. The kits of the invention typically comprise at least one container containing the platelets of the invention, and can further comprise optional components, such as sterile aqueous liquid for rehydrating the platelets, equipment for administering the platelets, and the like.

DETAILED DESCRIPTION OF VARIOUS EXEMPLARY EMBODIMENTS OF THE INVENTION

Figure 1:
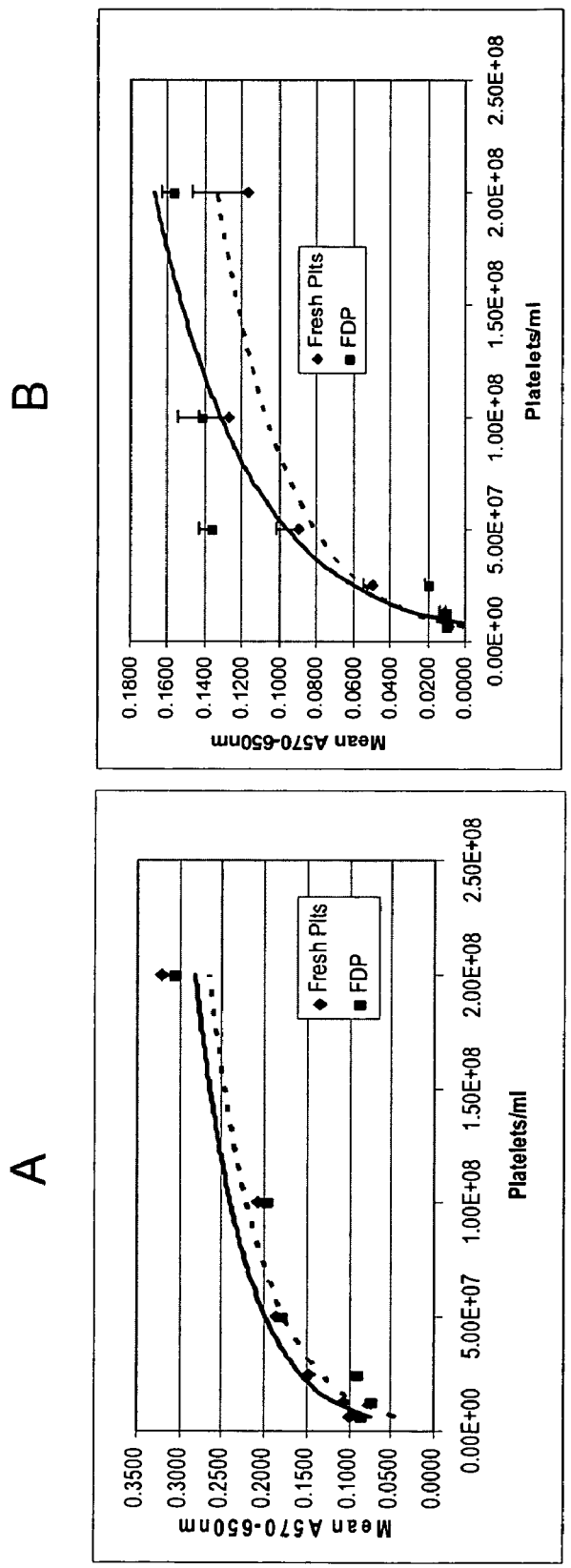
FIG. 1 depicts graphs showing the effects of freeze-dried platelets on the proliferation of fibroblasts (Panel A) and human umbilical vein endothelial cells (Panel B).

In a first aspect, the invention provides freeze-dried platelets, rehydrated freeze-dried platelets, and compositions comprising freeze-dried platelets or rehydrated freeze-dried platelets. The compositions can, but do not necessarily, comprise microparticles in addition to the platelets, and these microparticles can be included as a result of preparation of the freeze-dried platelets, or can be intentionally added as a component of the compositions.

Where the invention provides platelets, they can be provided in a dry form, for example as freeze-dried or lyophilized platelets. Alternatively, they can be provided as rehydrated freeze-dried platelets. In either case, depending on the method used to make the freeze-dried platelets, the platelets can have varying degrees of similarity to freshly-isolated platelets or platelets that have been stored for a short period of time, for example fewer than six days (in-dated platelets). In exemplary embodiments, the platelets retain all of the characteristics that are essential for platelet clotting function in the presence of normal platelets in blood. In other exemplary embodiments, the platelets are lacking or are deficient in one or more characteristic.

Freeze-dried platelets and rehydrated platelets derived from these freeze-dried platelets can be made from freshly isolated platelets (less than a few hours after removal from a donor subject's body) in-dated platelets (less than six days after removal from a donor subject's body), or out-dated platelets (six or more days after removal from a donor subject's body). It has surprisingly been found that out-dated platelets can be used as a source for freeze-dried platelets, and that such platelets, or rehydrated platelets derived from them, can be used not only for research purposes, but for treatment of bleeding as well.

Compositions according to the invention comprise platelets. The platelets can be freeze-dried platelets or rehydrated freeze-dried platelets. The compositions can comprise any number of substances in addition to platelets. Thus, a composition of the invention can be a solid or a liquid. When in the form of a liquid, the composition can comprise water or another aqueous solvent, such as an aqueous buffer, blood or a blood component or fraction (such as plasma), saline, buffered saline (e.g., phosphate buffered saline), or the like. Accordingly, rehydrated freeze-dried platelets of the invention can be rehydrated with any such liquid, including without limitation water, aqueous buffer, and blood or plasma. The liquid can also comprise one or more organic solvents, such as one or more alcohols. The compositions can be suitable for in vivo treatment of bleeding or bleeding disorders, can be suitable for in vitro or in vivo diagnostics, or can be suitable for in vitro or in vivo research.

The compositions comprising platelets can comprise one or more other substances in addition to the platelets. For example, they may comprise one or more substances that were present with the platelets before, during, or after the platelets were freeze-dried. Thus, the compositions comprising platelets can also comprise one or more salts, such as phosphate salts, sodium salts, potassium salts, calcium salts, magnesium salts, and any other salt that can be found in blood or blood products, or that is known to be useful in freeze-drying platelets or eukaryotic cells, or any combination of two or more of these. Other exemplary substances that may be present in the compositions include, but are not limited to, sugars, such as monosaccharides and disaccharides (e.g., maltose, dextrose, mannose, trehalose, sucrose, polymers of sucrose, glucose); polysugars, such as Ficoll-70 and Ficoll-400; glycerol; triglycerides; polysaccharides; lipids; dextran; polyvinyl pyrolidone (PVP); starch; hydroxyethyl starch (HES); and the like. Yet other exemplary substances include biological molecules derived from human or animal sources, such as polypeptides (e.g., albumins such as bovine serum albumin and human serum albumin), casein, laminin, fibrinogen, and the like. Of course, because the freeze-drying procedure can result in lysis of a certain number of platelets, compositions of the invention may comprise, external to intact platelets, some or all of the components present in the interior of a platelet.

One particular group of substances that may be present in a composition of the invention is chemical and biological compounds that function as drugs. Another group is substances that function as food. Yet another group is substances that function as herbal supplements. In embodiments, the substances are anti-coagulants. Compositions of the invention can, but do not necessarily, contain fibrin. Compositions according to the invention that do not contain fibrin can provide an advantage over compositions known in the art, for example when the compositions of the invention are used to treat non-compressible wounds.

In certain embodiments, compositions of the invention comprise platelets, microparticles, or both, but no other substance that is biologically active in forming a clot.

In embodiments, the compositions of the invention comprise platelet microparticles in addition to the platelets. In such embodiments, the platelets typically comprise about 10% to about 60% of the total number of particles, particularly platelet or platelet-derived particles, in the composition. For example, platelets can comprise about 10% to about 50% of the particles, about 20% to about 50% of the particles, or about 20% to about 40% of the particles. In embodiments, about 70% of the particles in the composition are retained when the composition is filtered through a mesh size that retains particles of the size of a typical platelet. Thus, in embodiments up to about 70% of the particles in the composition are platelets. Accordingly, the compositions of the invention can comprise 70% platelets and 30% microparticles, 60% platelets and 40% microparticles, 50% platelets and 50% microparticles, 40% platelets and 60% microparticles, 20% platelets and 80% microparticles, or 10% platelets and 90% microparticles. Of course, any particular specific whole number of platelets or microparticles within any of the ranges or amounts discussed above are contemplated by the invention. Because one of skill in the art would immediately recognize each of the numerous possible combinations of amounts of platelets and microparticles, it is not necessary to specifically disclose each herein.

The freeze-dried platelets can be used as an injectable or infusible substance for treatment of bleeding in a patient, or can be used as a direct treatment for bleeding that is accessible from outside the body. They likewise can be used for in vivo or in vitro diagnostic purposes or for in vivo or in vitro studies, such as for studies on the blood clotting process. The freeze-dried platelets, or rehydrated platelets made from them, can have properties of freshly obtained or in-dated platelets sufficient to provide clotting functions, and promote wound healing.

One advantage to embodiments of the freeze-dried platelets, rehydrated platelets, and compositions of the present invention is that platelet microparticles can accelerate clot formation, likely at least in part by way of their ability to promote tenase and prothrombinase activities, thereby enhancing thrombin-generating capacity and promoting rapid clot development at the injury site. In addition, due to the fact that the compositions can comprise a platelet-derived material and can contain a number of important growth factors, they can also contribute to the process of wound healing and tissue regeneration. Studies have found that mitogenic lipids and growth factors, such as platelet derived wound healing factors (PDWHF), platelet-derived growth factor (PDGF), transforming growth factor (TGF), and insulin growth factors (IGF), among others, are important in different stages of wound-healing cascade and greatly influence mitogenic and cellular differentiation activities. Thus, in embodiments, one or more of these factors are included in the compositions or provided in the methods of treating.

In another aspect, the invention provides methods of making freeze-dried platelets. The method generally comprises obtaining platelets, exposing the platelets to at least one saccharide under conditions that are sufficient for the saccharide to be taken into the platelets; adding a cryoprotectant to the platelets; and lyophilizing the platelets. The freeze-dried platelets can be re-constituted or re-hydrated (used interchangeably herein) by exposure to an aqueous liquid, such as water or an aqueous buffer. Alternatively, the freeze-dried platelet preparations can be used directly in methods of treating, diagnostic methods, or research methods. Specific exemplary methods for preparing freeze-dried platelets are provided in the Examples below.

In embodiments, the method comprises providing platelets, suspending the platelets in a salt buffer that comprises at least one saccharide to make a composition, incubating the composition at a temperature above freezing for at least a sufficient time for the at least one saccharide to come into contact with the platelets, adding a cryoprotectant to make a second composition, and lyophilizing the second composition.

The act of providing platelets can be any act that results in platelets being made available for use in the method in a form suitable for use in the method. Thus, providing can comprise removing blood from a subject and isolating or purifying (to any suitable extent) platelets from other blood components. Any known procedure for separating platelets from other blood components can be used. Accordingly, it can be through a process of obtaining platelets through plasmapheresis or sequential differential centrifugation of blood. For example, differential centrifugation can be used to isolate or purify platelets from other blood components through a two-step process in which blood is centrifuged at 3000×g for 45 minutes; platelet-poor liquid removed; the platelet-rich pellet resuspended in an aqueous buffer, and the mixture re-centrifuged at 200×g for 5 minutes to pellet the platelets. Alternatively, a single centrifugation step can be used, such as centrifugation at 100×g for 10 minutes. During the process of obtaining the platelets, one or more substances may be added to the compositions comprising the platelets, such as one or more anticoagulant or stabilizer. Other methods are known to those of skill in the art, and any such method can be used without undue or excessive experimentation.

The platelets may be from any source. Accordingly, they may be from an animal, such as a pig, horse, dog, cow, sheep, goat, rabbit, rat, mouse, monkey, or cat. They also may be from a human. In certain cases, the platelets may be provided as a mixture from two or more sources, such as a mixture of two or more units of blood obtained from random blood donors to a public blood bank. In other embodiments, such as embodiments where the platelets are intended to be used at a later date for infusion back into the donor, the platelets can be from a known source, and are thus considered autologous platelets for the purposes of the methods of treatment disclosed herein. More specifically, the platelets may be originally obtained from the ultimate recipient of the freeze-dried platelets or reconstituted platelets. In general, the platelets will be provided from a fresh source (i.e., in-dated platelets from blood obtained from a donor less than 6 days prior to freeze-drying), although out-dated platelets may be used in some situations, particularly for preparation of freeze-dried platelets intended for use as a hemostat to aid in stopping bleeding at a particular site of injury, and for in vivo and in vitro diagnostics or research.

The platelets that are provided are suspended in a salt buffer that comprises at least one saccharide, resulting in a platelet-containing composition. The salt buffer may be any buffer that maintains at least a majority of the platelets in an intact, functional state while in the buffer. Preferably, the buffer maintains the platelets at a pH of about 6.2 to about 7.8. Thus, the salt buffer may be an isotonic salt buffer comprising salts naturally encountered by platelets, such as those comprising sodium salts, potassium salts, calcium salts, and the like, and combinations of such salts. Alternatively, it may comprise one or more salts that platelets are not naturally in contact with. The identity of the salt(s) in the buffer are not critical so long as they are present in amounts that are not toxic to the platelets and maintain at least a majority of the platelets in an intact, functional state while in the buffer. Likewise, the buffering component may be any buffer that is non-toxic to the platelets and provides adequate buffering capacity to the composition at the temperatures at which the composition will be exposed during the method of the invention. Thus, the buffer may comprise any of the known biologically compatible buffers available commercially, such as HEPES, phosphate-buffered saline (PBS), and Tris-based buffers, such as TBS. Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl) imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); 1,40piperazinebis-(ethanesulfonic acid) (PIPES); N-(2-acetamido)-2-amnoethanesulfonic acid (ACES); 1,1-cyclohexanediacetic; 3,6-endomethylene-1,2,3, 6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propane-sulfonic acid (MOPS); phosphoric; N-tris(hydroxymethyl)methyl-2-aminoethane sulfonic acid (TES); and N-2-hydroxyethylpiperazine-N'-2-ethanesulfonic acid (HEPES). Furthermore, the buffer system can provide buffering capacity at the range of pH 4 to pH 8.

The salt buffer comprises at least one saccharide. The saccharide can be any suitable saccharide, including a monosaccharide or disaccharide or polysaccharide. The saccharide can be any saccharide that is compatible with maintenance of viability and function of platelets, and can be present in any amount that is not toxic to the platelets. In general, the saccharide can be any saccharide that is capable of passing through a cell membrane, such as the platelet membrane. Examples of suitable saccharides are sucrose, maltose, trehalose, glucose, mannose, xylose, Ficoll-70, and hydrogels having a molecular weight cut-off of less than about 100 kilodaltons. It is known that saccharides can be advantageously included in compositions for freeze-drying or lyophilizing platelets, and the present invention envisions use of at least one saccharide for stabilizing or otherwise promoting survival of platelets through the freeze-drying and reconstitution process. A preferred saccharide for use in the method of preparing freeze-dried platelets is trehalose. The saccharide may be present in the buffer in any suitable amount. For example, it may be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In certain particular embodiments, the saccharide is present in the buffer in an amount of at least or about any of the following concentrations: 40 mM, 50 mM, 60 mM, 70 mM, 80 mM, 90 mM, and 100 mM. Of course, in various embodiments, the saccharide is present in different specific concentrations within the ranges recited above, and one of skill in the art can immediately understand the various concentrations without the need to specifically recite each herein. Where more than one saccharide is present in the buffer, each saccharide may be present in an amount according to the ranges and particular concentrations recited above.

The salt buffer may comprise other components, as long as those components are non-toxic to the platelets at the concentration in which they are present in the buffer. Thus, polymers, such as proteins and polysaccharides, may be included in the buffer. Likewise, alcohols, such as ethanol, or polyalcohols, such as glycerols and sugar alcohols, may be included. Similarly, organic solvents, such as dimethyl sulfoxide (DMSO), can be included. Further, coagulation or platelet inhibitors, such as heparin, EGTA, citrate, and prostaglandin E (PGE).

In embodiments, the buffer comprises a cation-free HEPES-Tyrodes buffer (95 mM HEPES, 1 M NaCl, 48 mM KCl, 120 mM $NaHCO_3$) comprising 50 mM trehalose, pH 6.8. In other embodiments, the buffer comprises a cation-free HEPES-Tyrodes buffer comprising 100 mM trehalose and 1% (v/v) ethanol, pH 6.8.

The platelet-containing composition is incubated, at least in part to permit loading of the saccharide into the platelets. In general, the composition is incubated at a temperature above freezing for at least a sufficient time for the saccharide to come into contact with the platelets. Thus, incubation can be at 1° C., 4° C., 10° C., 20° C., 22° C., 25° C., 37° C., 42° C., 50° C., 55° C., or greater. In embodiments, incubation is conducted at 37° C. Furthermore, incubation can be performed for any suitable length of time, as long as the time, taken in conjunction with the temperature, is sufficient for the saccharide to come into contact with the platelets and, preferably, be incorporated, at least to some extent, into the platelets. In embodiments, incubation is carried out for at least or about 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes, or longer. In certain embodiments, incubation is performed at 20° C. to 42° C. for 100 minutes to 150 minutes. For example, in embodiments, incubation is performed at 35° C. to 40° C. (e.g., 37° C.) for 110 to 130 (e.g., 120) minutes. While incubation at higher temperatures than about 37° C. have been found to be suitable, it has been determined that such higher temperatures are unnecessary and, in embodiments, provide less than superior results. Furthermore, while incubation times greater than about 2 hours have been found to be suitable, it has been determined that such longer times are unnecessary and, in embodiments, provide less than superior results. Furthermore, reducing the time to 2 hours from, for example, 4 hours, reduces the time required to produce freeze-dried platelets, and provides an advantage for the practitioner over some other methods available in the art. In embodiments where activated platelets are desired, incubation times approaching or exceeding 4 hours in the presence of trehalose may be used. However, to reduce the amount of activation and minimize loss of structural integrity, incubation times of less than 4 hours, such as 2 hours, are more suitable.

Thus, the invention relates to methods of making platelets or compositions of the invention. In embodiments, the method of making the platelets or compositions generally comprises providing a material that contains platelets and/or microparticles, removing all or essentially all red blood cells that might be present in the material, adjusting the pH of the resulting red blood cell free material to an acidic pH, separating platelets, microparticles, or both from all or essentially all other components present in the material, resuspending the platelets, microparticles, or both in a liquid, and lyophilizing the platelets and/or microparticles. In embodiments, one or more agents that are typically included in lyophilization procedures, such as sugars, are added to the resuspended platelets and/or microparticles before lyophilizing. Exemplary sugars include, but are not limited to, monosaccharides, disaccharides (e.g., sucrose, lactose, maltose, isomaltose, cellobiose or trehalose), or polysaccharides. In embodiments, the method comprises sterilizing the lyophilized material using any known technique that is suitable for sterilizing lyophilized materials. In yet other embodiments, the method comprises heating the lyophilized platelets and/or microparticles.

For example, in an embodiment, the method can comprise making a composition comprising microparticles. The method can comprise: pre-activating platelets with platelet agonists such as TRAP, collagen, thrombin, or ionophores, then incubating the platelets for about 30 minutes at 37° C. Doing so activates the platelets prior to loading and lyophilization, which increases the relative percent of microparticles in the freeze-dried composition. A specific exemplary protocol for generating compositions with high relative proportions of microparticles (in this case, about 60-90% microparticles) comprises: collecting PRP into tubes; centrifuging at 1000×g for 15 minutes; decanting the supernatant; suspending the pellet in 10 ml PBS containing 10 mM EDTA, pH 6.5, washing in PBSE, pH 6.5; resuspending the pellet in PMP buffer (137 mM NaCl, 4 mM KCl, 0.5 mM $MgCl_2$, 0.5 mM $Na_2HPO_4$, 5.5 mM glucose, 10 mM HEPES, 2 mM $CaCl_2$) to achieve a platelet concentration of $2.5 \times 10^9$ platelets per ml; adding 15 uM SFLLRN and incubating at 37° C. for 10 minutes; centrifuging the remaining pellets at 750×g for 20 minutes; removing the supernatant and centrifuging it at 10,000×g at 4° C. for 30 minutes; removing the supernatant and resuspending the PMP in the same volume of 150 mM trehalose buffer (0.0095 M HEPES, 0.05 M NaCl, 0.0048 M KCl, 0.012 M $NaHCO_3$, 0.15 M trehalose, 0.005 M glucose, pH 6.8); adding ¼ volume of 30% ficoll, aliquotting liquid into 0.5 ml portions; and lyophilizing.

It is to be understood that the invention comprises practice of a single method for producing platelets, microparticles, or both. Each method may be adjusted to obtain the desired ratio of platelets to microparticles. It is also to be understood that the invention comprises practicing two or more different methods of producing freeze-dried platelets, each resulting in different ratios of platelets to microparticles, then combining the two resulting compositions in desired ratios to achieve the desired platelet to microparticle ratio.

Various modifications of the basic procedure, based on the parameters disclosed herein, can be made to either increase the relative amount of platelets as compared to microparticles, or to increase the relative amount of microparticles as compared to platelets. It has been found that increasing amounts of intact platelets improves the suitability of the compositions for in vivo infusion or injection treatment uses because the activation level of the composition is relatively low, and the composition shows a higher number of characteristics of normal, fresh or in-dated platelets. In contrast, where in vivo site-specific administration of clot-enhancing substances is desired, compositions comprising increasing amounts of microparticles are increasingly more desirable. It is believed that the increasing relative number of microparticles in the composition promotes faster clot times because it delivers increasing amounts of clot-promoting substances immediately, as compared to providing those substances by way of intact platelets, which might take extended periods of time to release them. Depending on the purpose of the diagnostic assay or research assay, one of skill in the art may select the appropriate method of making freeze-dried platelets to increase or limit the relative amount of microparticles in the composition comprising the freeze-dried platelets, or in the composition comprising rehydrated freeze-dried platelets.

In an additional aspect, the present invention provides a method of treating a subject in need of platelets or one or more platelet functions. In general, the method comprises obtaining platelets, platelet-derived microparticles, or both; and administering them to a subject (also referred to herein as a patient) in need of platelets or one or more platelet functions. An advantageous characteristic of this aspect of the invention is that it provides different embodiments that have different applications. For example, in embodiments, it provides methods of using the platelets, microparticles, and/or compositions to treat injuries or wounds involving bleeding, where the platelets, microparticles, and compositions are capable of being administered to a patient in need by direct application (such as by topical administration) rather than as an infusion of fresh or in-dated platelets, as is typical in the art. On the other hand, it provides methods of using the platelets, microparticles, and/or compositions to treat injuries or wounds involving bleeding, where the platelets, microparticles, and/ or compositions are capable of being administered to a patient in need by infusion or injection of the freeze-dried platelets, microparticles, or compositions, rather than by infusion of fresh or in-dated platelets, as is typical in the art.

The platelets, microparticles, and compositions will be those consisting of or comprising freeze-dried platelets or rehydrated freeze-dried platelets. To the knowledge of the inventors, for the first time, this invention provides use of freeze-dried platelets for in vivo therapeutic purposes. It also provides for use of rehydrated freeze-dried platelets for in vivo therapeutic purposes. Likewise, it provides for use of freeze-dried microparticles and rehydrated freeze-dried microparticles for in vivo therapeutic purposes.

Administering can be by direct application of the platelets or one or more compositions to a site of bleeding. Likewise, it can be by direct application of the platelets or one or more compositions to a site immediately adjacent to the site of bleeding. Thus, it can be by providing platelets, microparticles, or compositions in a bandage or other carrier, which can be placed in contact with the site of bleeding. It can also be by infusion of platelets or one or more compositions into the blood system of the subject being treated. Alternatively, it can be by injection of platelets or one or more compositions into the blood system of the subject being treated.

The methods of the invention can be used to treat wounds or injuries that involve bleeding. They also can be used in various other treatments, as mentioned herein. The bleeding can be due to anything, but is typically due to injury or other trauma (including surgery) or a bleeding disease or disorder. The methods can be used to completely stop bleeding by, for example, forming a clot at the site of bleeding, or they can be used to promote wound healing by reducing the amount of bleeding at a site, in some instances acting as an adjunct or aid in the clot forming process provided by the patient's blood system.

The methods can comprise the optional step of rehydrating the freeze-dried platelets and/or microparticles prior to administering them to the subject.

The subject or patient can be any subject in need of platelets or one or more platelet functions. For example, the subject can be one that is suffering from a bleeding wound or one who has a bleeding disease or disorder. The subject or patient can be an animal, such as a companion pet (e.g., dog, cat, rodent, bird) or a farm animal (e.g., cow, sheep, horse, goat, chicken). It can also be a laboratory animal, such as a rodent (e.g., rat, mouse), a rabbit, or a monkey. It can be a human. In general, it can be any animal, including, but not limited to, mammals.

The present invention includes the dual use of a mixture of freeze-dried, processed platelets and platelet microparticles, or rehydrated platelets and microparticles obtained or derived from them. Thus, in one facet, the compositions of the invention can be used as non-infusible hemostatic agents that can be used to rapidly stop bleeding in not only low pressure areas of the vasculature, but in high pressure areas as well, such as the abdominal aorta artery, femur artery, carotid artery, and other blood vessels that are not amenable to the current means of hemostatic controls, such as manual compression and/or tourniquet applications.

Various embodiments, the invention provides compositions and methods of treating that embody the concepts of: a composition comprising freeze-dried platelets, freeze-dried microparticles, or a combination of freeze-dried platelets and freeze-dried microparticles, and the use of such compositions, including derivatives and modifications thereof, in any form, including as freeze-dried powder, an aerosol system, vapor mists, bandages, and the like, for treatment of an injury or wound involving bleeding by applying the composition to the injury or wound; a composition and use thereof as a hemostat agent to arrest bleeding, including heavy bleeding, from low pressure and/or high pressure blood vessels such as, but not limited to, abdominal aorta arteries, coronary arteries, femur arteries, carotid arteries, hepatic arteries, celiac arteries, renal arteries, iliac arteries, and other blood major vessels, where the hemostat agent is administered directly at or near the site of bleeding, and not administered at a distant site, such as would be the case with infusion and systemic delivery of a composition; and a composition of the invention, derivatives and any modifications thereof, to be used as a non-infusible hemostat agent in a method of treatment to apply to surgical/trauma sites to decrease total blood loss and reduce the need for blood transfusions. The invention also provides compositions and methods of treating that embody the concepts of: a composition, derivatives and any modifications thereof, to be used as a non-infusible hemostat agent to apply to control bleeding in congenital or acquired coagulopathy; a composition, derivatives and any modifications thereof, to be used as a non-infusible hemostat agent to apply to control bleeding to patients on anti-thrombotic medications; a composition, derivatives and any modifications thereof, to be used as a sealant to be applied in invasive surgeries such as, but not limited to, splenic, hepatectomy, duodenopancreatectomy, and cholecystectomy, to control bleeding and accelerate tissue regeneration; a composition, derivatives and any modifications thereof, to be used as topical/wound healing application for pathological conditions, such as, but not limited to, diabetic ulcers, cutaneous ulcers, and other non-healing wounds. The invention further provides compositions and methods of treating that embody the concepts of: a composition, derivatives and any modifications thereof, to be used as an agent to accelerate topical wound healing; a composition, derivatives and any modifications thereof, to be used as an agent to reduce scar formation; a composition, derivatives and any modifications thereof, to be used as an agent for anastomosis indications; and a composition, derivatives and any modifications thereof, for the treatment of conditions that are associated with impaired or inappropriate angiogenesis, and diseases involving the vasculature or endothelial cells. These can be, but are not limited to, age-related macular degeneration, coronary artery disease, peripheral vascular disease, islet cell transplantation, fracture and tendon repair, reconstructive surgery, tissue engineering, restenonsis, cancer, diabetic retinopathy, rheumatoid arthritis, psoriasis, hemangiona/AEDS-related Kaposi's sarcoma, atherosclerotic plaque rupture, and the like. Thus, among many uses, the compositions of the invention can be used both as hemostatic agents and to accelerate the process of wound healing.

Accordingly, the present invention provides methods of using the platelets, microparticles, and compositions, such as methods of treating a subject in need of at least one blood clotting component, for the in vivo and in vitro purposes discussed herein.

In embodiments, the invention provides methods of treating subjects who are in need of, or are suspected of being in need of, one or more components of the clotting system of normal blood. Because the platelets of the invention provide at least one factor that is sufficient to overcome the deficiencies of forms of hemophilia and treatment-induced coagulopathy, the compositions of the invention can be used to treat individuals (i.e., subjects, patients) suffering from hemophilia or forms of coagulopathy. In general, the methods comprise administering the composition of the invention to an individual in an amount sufficient to raise the hemostatic properties of that individual's blood to a level that is detectably higher than it was before administration. Thus, the methods of the invention generally comprise administering a composition of the invention to an individual such that an amount of platelets sufficient to overcome the deficiencies of the disease or disorder afflicting the individual is delivered to the individual.

In embodiments, the methods treat individuals suffering from hemophilia. The hemophiliac can be suffering from Hemophilia A, Hemophilia B, Hemophilia C, or Acquired Hemophilia with Inhibitors. Likewise, any level of hemophilia (total, severe, or moderate) can be treated according to the methods of the invention.

In other embodiments, the methods treat patients who are undergoing treatment with anticoagulant agents or other agents or therapies that cause clotting systems to be compromised. Thus, in embodiments, the methods are methods of treating chemotherapy-induced blood clotting disorders, radiation-induced blood clotting disorders distinct from thrombocytopenia, or blood clotting coagulation disorders resulting from exposure to one or more detrimental environmental agents. It is preferred that the compositions of the invention are administered in amounts that result in platelet counts not exceeding the resting platelet count by two fold. In other words, if the recipient has a baseline count of 200,000 platelets/ul, then the product should be administered in doses of about $10^{11}$ platelets, this dose being designed to increase baseline counts by about 50,000 platelets/ul per dose. Two or more doses may be needed to achieve hemostasis, depending upon the nature, location, and severity of the bleed.

The methods of the invention can thus further comprise administering a composition of the invention a second or multiple times. Therefore, the methods of the invention encompass treatment regimens in which administration is repeated one or more times. Successive administrations may include the same amount of platelet derivatives or a different amount, and may include additional components or not. The choice of amounts and composition components can be selected by those of skill in the art based on various parameters, such as subject age, weight, medical history, clinical presentation, ancillary medical presentations, and the like. It is well within the skill of those in the art to make appropriate changes and adjustments to treatment regimens without undue experimentation. Thus, methods of the invention may comprise multiple administrations of compositions of the invention, each administration separated by a predetermined amount of time. For example, for prophylactic treatment of hemophilia, a composition of the invention may be administered once a week or once every two weeks. Other suitable regimens will be apparent based on the disease or disorder being treated.

The method can further comprise administering other biologically active agents, such as clotting factors, and chemotherapeutic agents for treatment of cancer. It can also comprise treatment with physical modalities, such as with radiation. There are numerous and varied additional treatments that will be evident to those of skill in the art, and any such treatments can be included in the methods of the present invention.

The present invention thus contemplates the use of the platelets of the invention for treatment of bleeding disorders, particularly those in which the patient's platelet counts are normal or not considered clinically abnormal. Thus, the invention contemplates the use of the platelets of the invention for treatment of all forms of Congenital Hemophilia, Hemophilia with Inhibitors, Acquired Hemophilia, and drug-induced coagulopathy. It further contemplates the use of the platelets for the neutralization of heparin, for example, during interventional cardiology procedures, and as an antidote for low molecular weight heparins and direct or indirect Factor Xa inhibitors. The invention is further applicable in the use of the platelets in an adjunctive therapy for enhancing the efficacy of recombinant Factor VIIa. It likewise finds use in the treatment of acquired Factor X deficiency, for example during light chain amyloidosis. It can also find use in treatment of coagulation factor deficiencies other than that of Factor II (prothrombin) or Factor I (fibrinogen). The invention and disclosed platelets may also find use in treatment of transient coagulopathy occurring as a result of hepatic dysfunction, such as that associated with liver failure or liver transplantation, and as a result of kidney failure, which can result in uremia. Additional applications of the platelets of the invention include use in treatments (e.g., as an antidote) for GPIIb/IIIa antagonist therapy and in treatment of vWD.

One aspect of the invention is the use of non-autologous blood products as the source for the compositions of the invention. More specifically, platelet-based hemostat products currently available for use in treating bleeding use blood drawn from the patient in need of the treatment (i.e., autologous blood donations). The present invention does not require autologous donation of the source for the compositions of the invention. Indeed, the present invention need not even rely on fresh or in-dated platelets. That is, it has been surprisingly discovered that out-dated platelets, such as those between six and nine days post-donation, can provide suitable platelet functions when provided as freeze-dried platelets, freeze-dried platelet compositions (which can or might not comprise significant amounts of microparticles), or compositions comprising rehydrated freeze-dried platelets.

In view of the methods of the invention, the invention provides for the use of the compositions of the invention in the preparation of therapeutically effective compositions or formulations. These compositions or formulations can be used to treat bleeding as well as to treat hemophilia or other diseases or disorders that result in lack of normal clotting, or that involve low or absent levels of one or more clotting factors. Accordingly, the invention provides for the use of the compositions or formulations of the invention in the treatment of hemophilia or other diseases or disorders characterized by low or absent levels of one or more clotting factors. Other non-limiting exemplary embodiments include the use of platelet derivatives for the treatment of bleeding diathesis associated with liver damage, liver failure, or liver transplantation, as well as kidney failure (uremia).

In another aspect, the present invention provides methods of using the freeze-dried platelets or reconstituted platelets derived therefrom for diagnostic or research purposes. The methods of diagnosis are typically performed in vitro, but may be performed in vivo on test animals if desired. The methods of diagnosis generally are performed to identify bleeding disorders and causes of those disorders. Research methods generally relate to discovery of causes of bleeding disorders, such as the molecular basis for a particular person's inability to normally control bleeding in response to wounds or other injuries. The research methods can also relate to study of the effects of drug treatments on the blood clotting system of individuals (e.g., side effects that negatively affect blood clotting) or on the process of blood clotting in general or specifically in regard to one or more particular steps in the process.

In methods of diagnosis, the methods can be methods of diagnosing a disease or disorder of the blood clotting system. These methods generally comprise obtaining freeze-dried platelets, combining the freeze-dried platelets with platelets and/or plasma removed from a patient having, or suspected of having, a disease or disorder of the blood clotting system to form a mixture, and determining whether the person has a defect in the blood clotting system by assaying one or more biological or biochemical functions of the mixture, where the defect decreases or abolishes the patient's blood clotting system's ability to function normally or to cause clot formation in a pre-defined period of time. Typically, determining whether the patient's blood clotting system is defective comprises assaying clotting time of the mixture. The freeze-dried platelets may be rehydrated prior to use.

In certain applications, the methods can be methods of monitoring the progression of a disease or disorder of the blood clotting system. These methods generally comprise obtaining freeze-dried platelets, combining the freeze-dried platelets with platelets and/or plasma removed from the patient suffering from the disease or disorder to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of progression over time. The freeze-dried platelets may be rehydrated prior to use.

The methods may also be methods of monitoring the effects of a treatment regimen for a patient on the blood clotting system of that patient. In general, these methods comprise obtaining freeze-dried platelets, combining the freeze-dried platelets with platelets and/or plasma removed from the patient undergoing the treatment regimen to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time. The freeze-dried platelets may be rehydrated prior to use.

In yet another aspect, the invention provides kits. In general, a kit of the invention comprises the freeze-dried platelets of the invention. The kit can be configured to supply the freeze-dried platelets for use in in vivo treatments, for use in in vitro diagnostics, or for use in in vitro or in vivo research. The kits of the invention typically comprise at least one container containing the platelets of the invention, and can further comprise optional components, such as sterile aqueous liquid for rehydrating the platelets, equipment for administering the platelets, and the like.

In its most basic form, a kit of the invention is a container comprising platelets (freeze-dried or reconstituted) or at least one composition according to the invention. The container can be any material suitable for containing the composition of the invention, such as a vial or ampule. It can be fabricated from any suitable material, such as glass, plastic, metal, or paper or a paper product. In embodiments, it is a glass or plastic ampule or vial that can be sealed, such as by a stopper, a stopper and crimp seal, or a plastic or metal cap such as a screw cap. In general, the container and seal are made of materials that can be sterilized by heat (dry or wet), radiation (UV, gamma, etc.), or exposure to chemicals. Preferably, the container is sterilized before the composition of the invention is introduced into the container. Typically, the container will be of sufficient size to contain the composition of the invention, yet have head space to permit addition of additional substances, such as sterile water or saline or a mixture of the two, which can be used to rehydrate the composition in the container. In embodiments, the container comprises a sufficient amount of platelet derivatives to perform a method according to the invention. Thus, in embodiments, the container contains a sufficient amount of platelet derivatives for one dosage, two dosages, or even more, for treatment of an individual suffering from bleeding or a bleeding disorder. The amount of platelet derivatives contained in the container can be selected by one of skill in the art without undue experimentation based on numerous parameters, including, but not limited to, the weight of the patient, the type of bleeding or bleeding disorder being treated, the number of dosages to be administered in a given amount of time (e.g., in the 24 hour period following hydration of the composition).

In embodiments, the container is provided as a component of the kit, which includes suitable packaging and, optionally, instructions and/or other information relating to use of the compositions. Typically, the kit is fabricated from a sturdy material, such as cardboard or plastic, and can contain the instructions or other information printed directly on it. In embodiments, the container or kit comprises other components, such as one or more purified components of the clotting cascade, one or more applicators, one or more coverings or coatings for the site of administration of the platelets, an the like. The kit can comprise multiple containers containing the composition of the invention. In such kits, each container can be the same size, and contain the same amount of composition, as each other container. Alternatively, different containers may be different sizes and/or contain different amounts of compositions or compositions having different constituents. One of skill in the art will immediately appreciate that numerous different configurations of container sizes and contents are envisioned by this invention, and thus not all permutations need be specifically recited herein.

In general, the kit comprises at least one container to contain the components of the kit, and is considered a single package comprising a combination of containers. Thus, the components are said to be in packaged combination within the kit. In addition to a container containing the platelets or composition of the invention, the kit can comprise additional containers containing additional platelets or compositions of the invention. Each container may contain enough platelets for a single dosage for treatment, or it may contain two or more dosages. The various containers may contain differing amounts of the platelets and/or compositions of the invention. Thus, in embodiments, the kit comprises a sufficient amount of platelets to perform a method according to the invention. In embodiments, the kit comprises other components, such as purified components of the clotting cascade, etc. The kit can further comprise some or all of the supplies and materials needed to prepare and administer the compositions of the invention, such as large-bore needles and syringes, pumps, sterile cloths and solutions for sterilizing sites of injection, etc. In embodiments, the kits comprise one or more liquid to hydrate the compositions of the kits. The liquid may be any suitable liquid, but is typically a water-based liquid, such as water, saline, or a mixture of the two.

Although any suitable amount of platelets may be provided in each particular container in a kit, or in a kit in total, for in vivo therapeutic purposes in which platelets are administered directly to a site of bleeding, the kit will typically comprise at least one container containing at least or about $1 \times 10^8$ to $1 \times 10^{11}$ platelets. In embodiments, at least one container contains at least or about $1 \times 10^8$ platelets, $1 \times 10^9$ platelets, $1 \times 10^{10}$ platelets, or $1 \times 10^{11}$ platelets. For in vivo therapeutic purposes in which platelets are administered as an infusible or injectable hemostat, at least one container typically will contain at least about $1 \times 10^8$ to $1 \times 10^9$ platelets. Likewise, for in vitro diagnostic or research purposes, at least one container typically will contain at least about $1 \times 10^8$ to $1 \times 10^9$ platelets. It is to be noted that the amounts mentioned above are typical amounts for each container, and other amounts, higher or lower, are also contemplated.

EXAMPLES

Details of particular embodiments of the invention will be further clarified by the following examples, which are intended to be purely exemplary of the invention, and should not be considered as limiting the invention in any way.

Example 1

Preparation of a Composition of the Invention

Non-autologous platelets were purchased from BRT Labs (Baltimore, Md.) and used within 4-24 hours of draw. Platelet Rich Plasma (PRP) was obtained by low speed centrifugation (135×g) for 15 minutes to remove red blood cells. The centrifuged PRP (without red blood cells) was acidified to pH 6.5 by adding 1/14 volumes of ACD (acid citrate dextrose) and then pelleted by centrifuge at 1000×g for 10 minutes. The platelet-poor plasma was decanted, and the packed cells were drained over a paper towel to remove plasma proteins. Alternatively, residual liquid was removed by aspiration with a plastic transfer pipette. The platelets were resuspended in 1 ml of Cation-Free Tyrodes Buffer containing 50 mM of trehalose at pH 6.8, and the platelet concentration was adjusted to ~$1.0 \times 10^9$/ml. The mixture was incubated for 2 hours at 37° C., mixing once each half hour. Finally, the albumin (BSA) concentration was adjusted to 5% (w/v) of the platelet preparation for lyophilization. The lyophilization was performed using the following cycles:

TABLE 1

Lyophilization Protocol

| Period | Time (h) | Shelf Temp (° C.) Start | Shelf Temp (° C.) End | Vacuum (mTorr) |
|---|---|---|---|---|
| 1 | 0.63 | 30 | −45 | ambient |
| 2 | 4 | −45 | −45 | ambient |
| 3 | 1 | −45 | −40 | 100 |
| 4 | 12 | −40 | −30 | 100 |
| 5 | 12 | 30 | 30 | 100 |

The resulting lyophilized composition was irradiated at 0, 5, 30, and 50 kGy, packed, and sealed for various applications.

Example 2

Alternative Method for Making Freeze-Dried Platelets

A method of preparing freeze-dried platelets was developed to provide platelets having a long shelf-life and suitable characteristics upon rehydration. The method was found to provide freeze-dried platelets, and platelets reconstituted from those freeze-dried platelets, with advantageous properties for in vitro studies and in vivo therapeutic applications.

The method of preparing freeze-dried platelets comprised the following:

An initial saccharide-loading process included:
all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were ejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

platelets were divided equally into different centrifuge bottles;

where necessary, red blood cells (RBC) were removed by centrifugation in a fixed angle centrifuge at 500×g for 5 minutes—platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 5% of the volume of the platelet poor plasma removed in the previous step) of Loading Buffer (9.5 mM HEPES; 100 mM NaCl; 4.8 mM KCl; 5.0 mM glucose; 12 mM NaHCO$_3$; 50 mM trehalose; pH 6.8);

the resuspended platelets were measured for platelet counts, and the concentration adjusted to approximately 1250 ($1.25 \times 10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, human serum albumin was added to a final concentration of 5% (w/v);

the final platelet concentration was measured on the ACT-10 machine; and the platelet composition was lyophilized as indicated in Table 1, above;

Example 3

Alternative Method for Making Freeze-Dried Platelets with an Increased Percent of Microparticles A method of preparing freeze-dried platelets was developed to provide platelets having a long shelf-life and suitable characteristics upon rehydration. The method was found to provide freeze-dried platelets, and platelets reconstituted from those freeze-dried platelets, with advantageous properties for in vitro studies and in vivo therapeutic applications and having a high percentage of microparticles.

The method of preparing freeze-dried platelets comprised the following:

An initial saccharide-loading process included:

all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

platelets were divided equally into different centrifuge bottles;

where necessary, red blood cells (RBC) were removed by centrifugation in a fixed angle centrifuge at 500×g for 5 minutes—platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 5% of the volume of the platelet poor plasma removed in the previous step) of Loading Buffer (9.5 mM HEPES; 100 mM NaCl; 4.8 mM KCl; 5.0 mM glucose; 12 mM $NaHCO_3$; 50 mM trehalose; pH 6.8);

the resuspended platelets were measured for platelet counts, and the concentration adjusted to approximately 1250 ($1.25 \times 10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, human serum albumin was added to a final concentration of 5% (w/v);

the final platelet concentration was measured on the ACT-10 machine;

the platelet concentration was subjected to a quick freeze by immersing into liquid nitrogen (−190° C.) for 60 seconds; and the platelet composition was lyophilized as indicated in Table 1, above.

Example 4

Alternative Method for Preparation of Freeze-Dried Platelets

Another method of preparing freeze-dried platelets was developed to provide platelets having a long shelf-life and suitable characteristics upon rehydration. The method was found to provide freeze-dried platelets, and platelets reconstituted from those freeze-dried platelets, with highly advantageous properties for in vitro studies and in vivo therapeutic applications.

The method of preparing freeze-dried platelets comprised the following:

An initial saccharide-loading process included:

all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

where necessary, red blood cells (RBC) were removed by centrifugation in a fixed angle centrifuge at 500×g for 5 minutes—platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 10% of the volume of the platelet poor plasma removed in the previous step) of Loading Buffer (9.5 mM HEPES; 100 mM NaCl; 4.8 mM KCl; 5 mM glucose; 12 mM $NaHCO_3$; 50 mM trehalose; pH 6.8);

the resuspended platelets were measured for platelet counts, and the concentration adjusted to approximately 1250 ($1.25 \times 10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, Ficoll 400 was added to the platelets to give a final concentration of 6% (w/v);

the final platelet count was measured on an ACT-10 machine (the count typically was approximately 1000 ($1 \times 10^9$/ml);

the platelets were aliquotted and lyophilized using the same lyophilization protocol described in Table 1.

After lyophilization, the vials in which the platelets were lyophilized were stoppered under vacuum, capped immediately, and baked in an oven at various temperatures and times.

Where desired, the platelets were rehydrated with the same volume as the pre-lyophilization volume of the rehydration buffer added to the dried platelets. For example, if 1 ml of composition was lyophilized, then 1 ml of reconstitution buffer was added for rehydration.

The rehydration process usually involved the addition of distilled water; 6% Ficoll-400 in distilled water, 6% Ficoll-400, 2 mM Calcium Chloride, or 6% Ficoll-400, 2 mM Calcium Chloride, 1 mM Magnesium Chloride in distilled water.

The rehydrated platelets were allowed to equilibrate at room temperature for 30 seconds to 300 seconds before use.

Example 5

Comparative Example of Method Used in the Art to Produce Freeze-Dried Platelets To produce freeze-dried platelets for comparison to those made according to embodiments of the present invention, a protocol known in the art was used to make freeze-dried platelets. The method included:

PRP were obtained by centrifugation of blood (in CPD or CPDA anticoagulant solution) at 320×g for 14 minutes using a swinging bucket rotor and no centrifugation breaking;

PRP were removed and transferred to fresh tubes, taking care to avoid contamination with RBC;

$PGE_1$ in ethanol was added to 10 ug/ml from a 100× stock, and platelets were counted;

platelets were centrifuged at 480×g for 25 minutes;

the platelet-poor supernatant was removed by aspiration;

platelets were resuspended to a concentration of $1 \times 10^9$/ml in Tyrodes Phosphate Buffer, pH 6.8 containing 5 mM glucose and 40 mM trehalose, with 2 mM $Mg^{2+}$ plus 10 ug/ml PGE1 (added at 1:100 from 1 mg/ml stock) (i.e., 4.63 mM $Na_2HPO_4$, 5.37 mM $NaH_2PO_4$, 120 mM NaCl, 2.67 mM KCl, 2 mM $NaHCO_3$, 5 mM glucose, 2 mM $MgCl_2$, 40 mM trehalose, pH 6.8 (+10 ug/ml PGE1 from 1 mg/ml stock in EtOH);

a small amount was saved for further assay, if desired;

the sample was incubated 4 hours at 37° C., mixing by gentle inversion every half hour;

a sample was removed, where desired, for functional testing (e.g., aggregometry and FACS);

the composition was centrifuged at 480×g for 15 minutes;

the supernatant was removed by aspiration;

the pellet was resuspended to $1-2 \times 10^9$ platelets/ml in isotonic HEPES saline containing 5% Human Serum Albumin, 100 mM Trehalose, and 1 mM $MgCl_2$, pH 6.8 (i.e., 9.5 mM HEPES, 75 mM NaCl, 4.8 mM KCl, 1.00 mM $MgCl_2$, 100 mM trehalose, 5% Human Serum Albumin, pH 6.8);

platelets were counted on an ACT-10 machine, and the platelet count and volume recorded;

where desired, a sample was removed and saved for later testing (e.g., functional testing);

platelets were transferred to lyophilization vials with stopper caps and the contents of each vial weighed;

platelets were lyophilized using the same lyophilize cycle from Table 1;

lyophilized platelets were sealed in the lyophilization vials under vacuum;

lyophilized platelets were stored at ambient temperature or at 2-8° C. in the absence of dessicant; and where desired, the freeze-dried platelets were rehydrated with sterile water as follows: volume of water to add=weight of vial prior to lyophilization minus the weight of the vial after lyophilization, assuming 1 ml of water=1.0 g.

Example 6

Cell-Based Proliferation Assay

Fibroblast and endothelial cell proliferation assays were performed using a composition prepared according to Example 2. Briefly, freeze-dried platelets were made as follows: platelets were collected into acid citrate dextrose (ACD) anticoagulant buffer (1.5 volumes+8.5 volumes blood). Platelet Rich Plasma (PRP) was obtained by low speed centrifugation (135×g for 15 minutes) to remove red blood cells. The PRP was acidified to pH 6.5 by adding 1/14 volume of ACD and then pelleted by centrifugation at 1000×g for 10 minutes. The platelet pellet was resuspended in 1 ml of Cation-Free Tyrodes Buffer containing 50 mM trehalose, pH 6.8, and adjusted to ~$1.0 \times 10^9$ platelets/ml. The mixture was incubated for 2 hours at 37° C., mixing once each half hour. Finally, albumin was added to a final concentration of 5% of the total platelet preparation volume, and the platelet preparation was lyophilize.

Fibroblasts and Human Umbilical Vein Endothelial Cells (HUVECS) at passage 3 and 7, respectively, were starved for 24 hours using medium without Fetal Bovine Serum supplement. After 24 hours, the cells were passaged and seeded at 10,000 cells/well in a 96 well flat bottom dish, and allowed to attach for 2-3 hours. Once the cells were attached, the samples were added and incubated in a 37° C., 5% $CO_2$ humidified incubator for 48 hours. At 48 hours, the proliferation of the cells was measured by the MTT assay (ATCC), in which the cells reduced MTT dye that could be measured by the absorbance at 590-650 nm. Briefly, MTT dye was added to the well at a 1:10 ratio, and the plate was incubated at 37° C., 5% $CO_2$ humidified incubator for 2-3 hrs. After incubation, 100 ul of detergent was added and the optical density was determined at 590-650 nm. The numerical values obtained from A590-650 readings were used as a reference proliferation index.

The results of the proliferation assay are presented in FIG. 1, which shows that the freeze-dried platelets of the invention had essentially the same effect on proliferation of fibroblasts and endothelial cells as fresh platelets.

Example 7

Collagen-Fibroblast Contraction Assay

To even further characterize the platelets produced in Example 1, a collagen contraction assay was performed using those platelets. For the collagen contraction assay, fibroblast cultures at 80% confluence were harvested by treatment with 0.05% trypsin/0.02% EDTA. Trypsin was inactivated by addition of soybean trypsin inhibitor in PBS containing 0.2% BSA. The cells were washed twice with DMEM+10% FBS and resuspended at a concentration of $1 \times 10^6$ cells/ml. The fibroblasts were mixed with 10% FBS, neutralized collagen and concentrated DMEM so that the final concentration of DMEM and sodium bicarbonate was 1×. In some experiments, FBS was replaced by 30 ng/ml PDGF-BB and 2% BSA or dilutions of a reconstituted composition of the invention and 2% BSA. Samples (0.6 ml) of the cell mixture were added to the wells of a 24-well tissue culture plate, which was pre-coated with 2% BSA, and the collagen was allowed to polymerize at 37° C. The final concentration of collagen was about 1.8 mg/ml and each gel contained $6 \times 10^4$ cells. After two hours incubation, the gels were gently detached from the plastic surface to allow contraction, 0.5 ml DMEM+10% FBS per each well was added, and the gels were incubated overnight at 37° C. in 5% $CO_2$. If the collagen gels were contracted by the addition of PDGF-BB, the added medium was supplemented with 30 ng/ml PDGF-BB+2% BSA instead of FBS.

Figure 2:
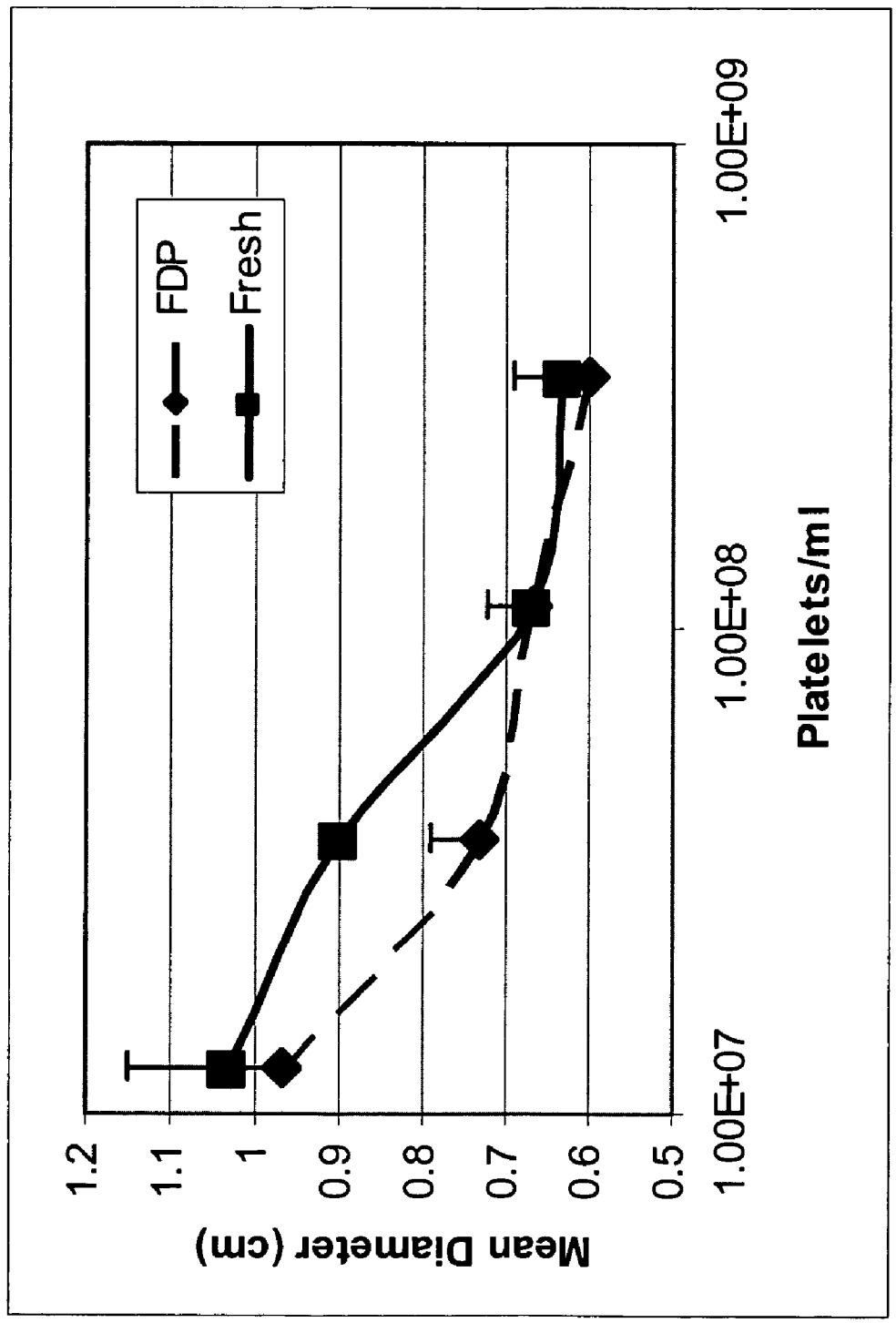
FIG. 2 depicts a graph of results of collagen contraction assays of collagen-fibroblasts matrix remodeling using freeze-dried platelets of the invention.

The results of the collagen contraction assay are depicted in FIG. 2. More specifically, FIG. 2 shows a graph of collagen-fibroblasts matrix remodeling using freeze-dried platelets of the invention. When a mixture of rat tail type I collagen and fibroblasts were incubated in media alone (control), platelet rich plasma (fresh platelets), or a composition (FDP) according to the invention made using example 2, samples containing the composition of the invention, FDP, and fresh platelets demonstrated collagen re-modelling and contraction, whereas, the control samples showed no contraction.

The experiments depicted in FIG. 2 were conducted to assess the effect of a composition of the invention on wound healing and remodeling. Although it is hard to show tissue remodeling in vitro, culturing of fibroblasts in three-dimensional native type I collagen gels have been used to demonstrate scar formation and tissue remodeling in wound healing. A number of studies previously showed that PDGF and fresh platelet could promote contraction of collagen gels in vitro. As shown in FIG. 2, the composition of the invention, promoted collagen contraction within 24 hours incubation. Thus, a composition of the invention promotes collagen matrix reorganization and fibroblast proliferation, and can achieve, facilitate, or assist in wound healing.

Example 8

Evaluation of the Physical Characteristics of a Composition

The structural composition of a composition prepared according to Example 1 was examined using the Beckman Multisizer 3 COULTER COUNTER (Fullerton, Calif.), particularly to analyze particle size. The multisizer provides size and volume distributions with a range up to 10 um. As used herein, the volume of a platelet is 2-4 um where as anything less than 1 um is considered to be platelet microparticles.

Figure 3:
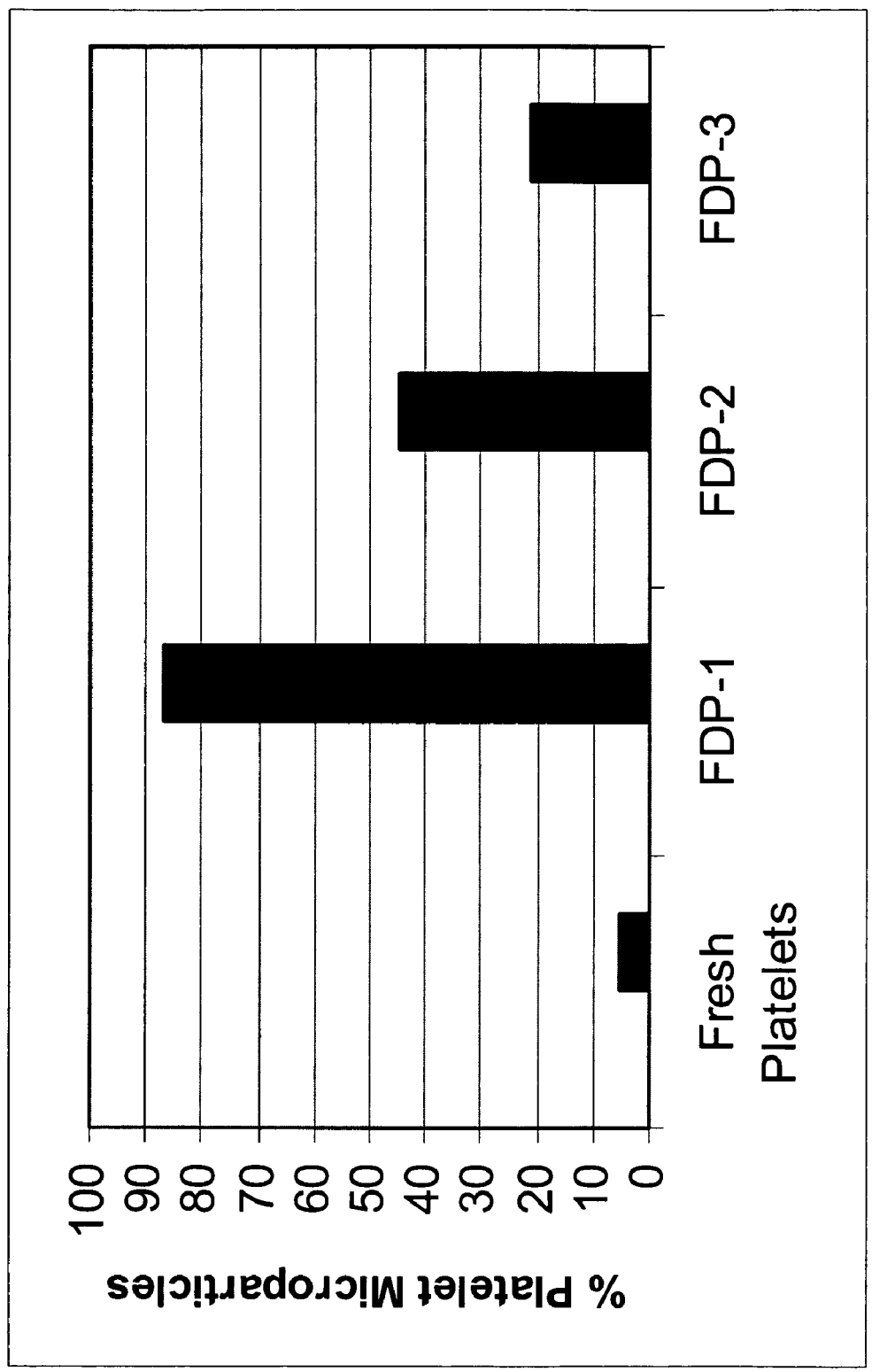
FIG. 3 depicts a graph showing the effect on microparticle concentration of three different protocols for preparing freeze-dried platelets.

FIG. 3 shows a graph of multisizer analysis of the platelet preparation. It shows that the composition is composed of percentage of platelet microparticles within the platelet preparation using Examples 2 and 3. As can be seen from FIG. 3, approximately 10-50% of the total number of particles produced by the method outline in Example 2 are microparticles (samples labeled FDP-2 and FDP-3), whereas, greater than 70% of the total number of particles produced by the method outline in Example 3 are microparticles (FDP-1). Thus, this Example shows that a composition according to the invention, either expose to extreme cold before lyophilization and upon reconstitution with water, showed a mixture of platelet microparticles and intact platelets.

Additionally, the expression of GPIIb/IIIa and other platelet surface markers can be detected on the surface of the platelets and microparticles (data not shown), in the samples made according to Examples 2 and 3, which mediated the binding of components of the composition to solid surfaces coated with fibrinogen in a reversible and specific manner (data not shown).

Example 9

Clotting Function of Freeze-Dried Platelets

To further characterize a composition of the invention, the freeze-dried platelets made by Examples 2 and 3 were tested for their ability to provide clotting functions.

Figure 4A:
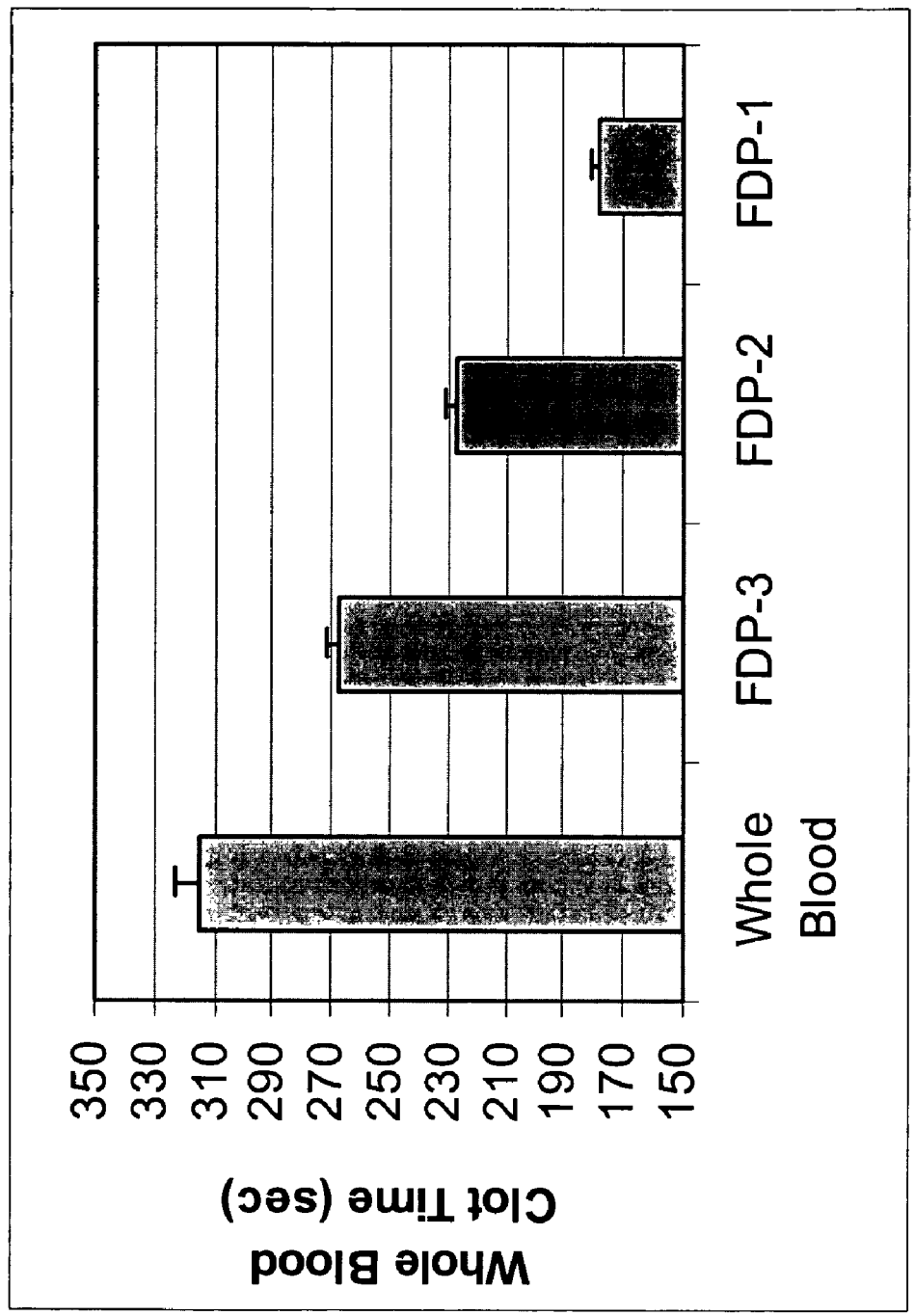
FIG. 4 depicts graphs showing the beneficial effect of higher microparticle concentrations on topical wound healing. Panel A shows the effect of microparticle concentration on clot time of whole blood. Panel B shows the effect of microparticle concentration on plasma.

FIG. 4A depicts the effect of freeze-dried platelets that contained different amounts of microparticles, as depicted in FIG. 3, on the clotting ability of whole blood samples. The data shown in FIG. 4A was obtained as follows: clot time was determined for a mixture containing 400 ul of ACD whole blood, 25 ul of 0.2 M $CaCl_2$, 25 ul saline, and 50 ul for various concentrations of reconstituted (rehydrated) freeze-dried platelets using samples FDP-1, FDP-2, and FDP-3.

As can be seen from FIG. 4A, the results of the whole blood assays showed that the FDP-3 sample, which contained the highest amount of microparticles, provided the shortest clot times, as compared to samples FDP-2 and FDP-3, which contained lower percentages of microparticles.

Figure 4B:
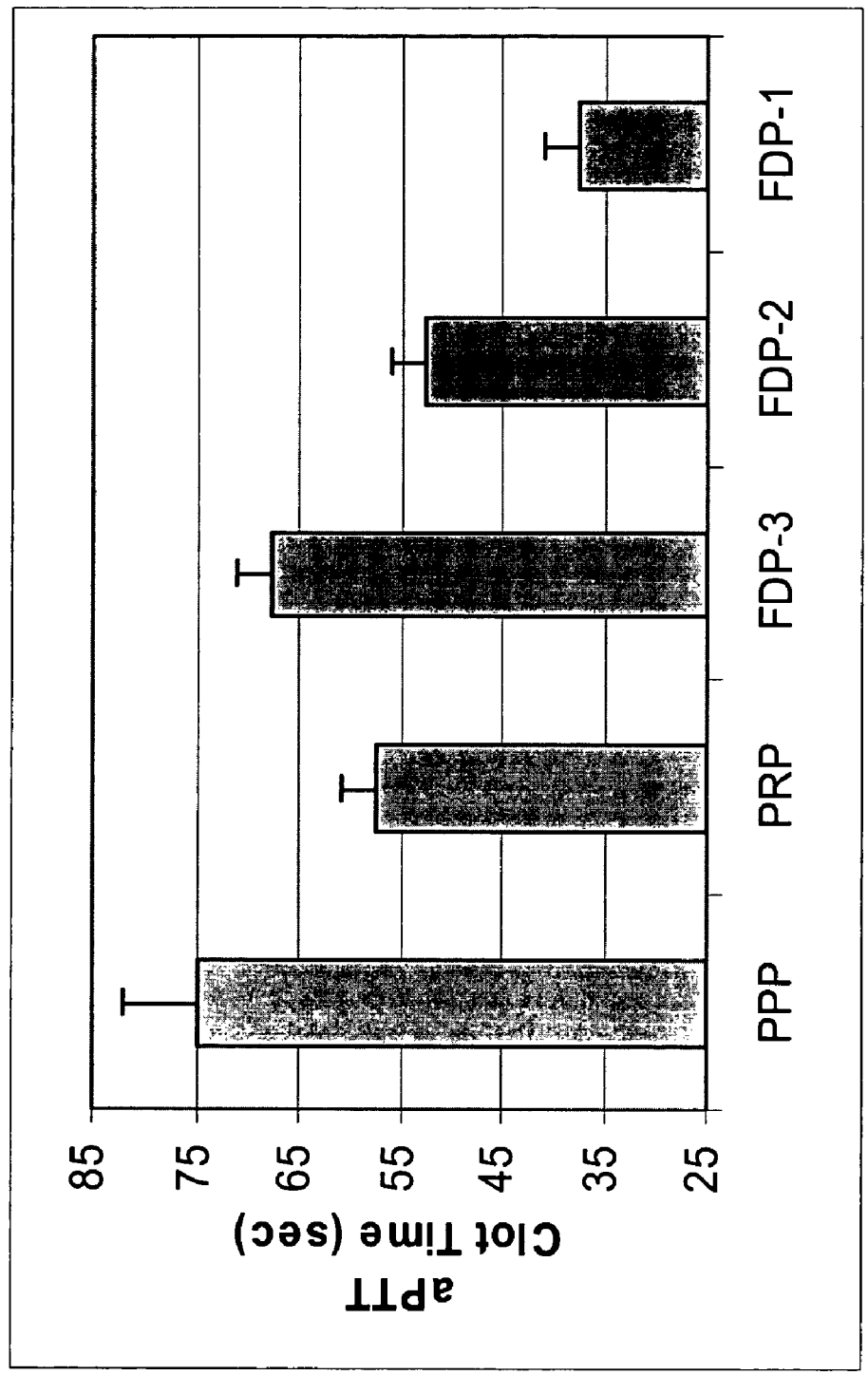

FIG. 4B depicts the effect of freeze-dried platelets that contained different amount of microparticles, as depicted in FIG. 3, on the clotting ability of normal pooled plasma samples. To assay clotting time, 100 ul of APCT (activated plasma clot time, Analytical Control Systems, Inc., Fishers, Ind.) reagent was mixed with 25 ul of various concentrations of water-reconstituted freeze-dried platelets from different preparations, FDP-1, FDP-2, or FDP-3, and 25 ul of factor-deficient plasma obtained from commercial suppliers. The mixture was incubated at 37° C. in a water bath for 3 minutes, then 100 ul of 0.02 M $CaCl_2$ (37° C.) was added, and clot time determined.

As can be seen from FIG. 4B, the results of the plasma based assays showed that the FDP-3 sample, which contained the highest amount of microparticles, provided the shortest clot times, as compared to samples FDP-2 and FDP-3, which contained lower percentages of microparticles.

Example 10

In Vivo Studies Using a Composition of the Invention

An experiment was conducted to investigate the hemostatic ability of a composition of the invention, and compare this to the widely use Quikclot™ and Surgicel™ products. The experiment was conducted at Qual Tech Labs, NJ. Sprague Dawley rats were obtained from Hilltop Lab Animals for the study. The test animals were male, adults, same age, and around 350 g in weight. Upon arrival, the animals were placed in quarantine for 48 hours, after which, the animals were housed in pairs in polypropylene cages with wire lids meeting NIH requirements. Animal room temperatures were recorded daily. A 12 hour light/dark cycle was maintained. Purina Rodent Chow and tap water were provided ad lib, except the food was withheld overnight prior to the study. Studies were performed in rats subjected to anesthesia with a 7:1 mixture of Ketamine/Xylazine, which was administered intramuscularly at 0.05 ml/100 grams body weight. Each test animal was placed on a surgery board and secured. The hair on the neck and abdomen were removed and the surgical sites swabbed with betadine. Then, the carotid artery was exposed and isolated. Using suture silk, the artery was tied off arterioly and clamped as far as it is practicable from the tie-off. The artery was catheterized between the tie-off and clamp with a 20 gauge catheter placement unit. The catheter was secured and connected to a WECO blood pressure monitor. The clamp was removed and the blood pressure allowed to stabilize. A midline incision approximately 20 mm long was made in the abdominal wall. The abdominal artery was isolated and suture silk was passed beneath the artery to facilitate location during the study. After that, puncture of the abdominal aorta was made using a 23 gauge needle. Various hemostatic agents, including a composition of the present invention, were applied onto the bleed site. This was compared to the control group. Survival was assessed and vital signs, such as systolic blood pressure, heart-rate, and oxygen saturation, were monitored over a 30-minute period. The rodents were euthanized at the end of the study.

Figure 5:
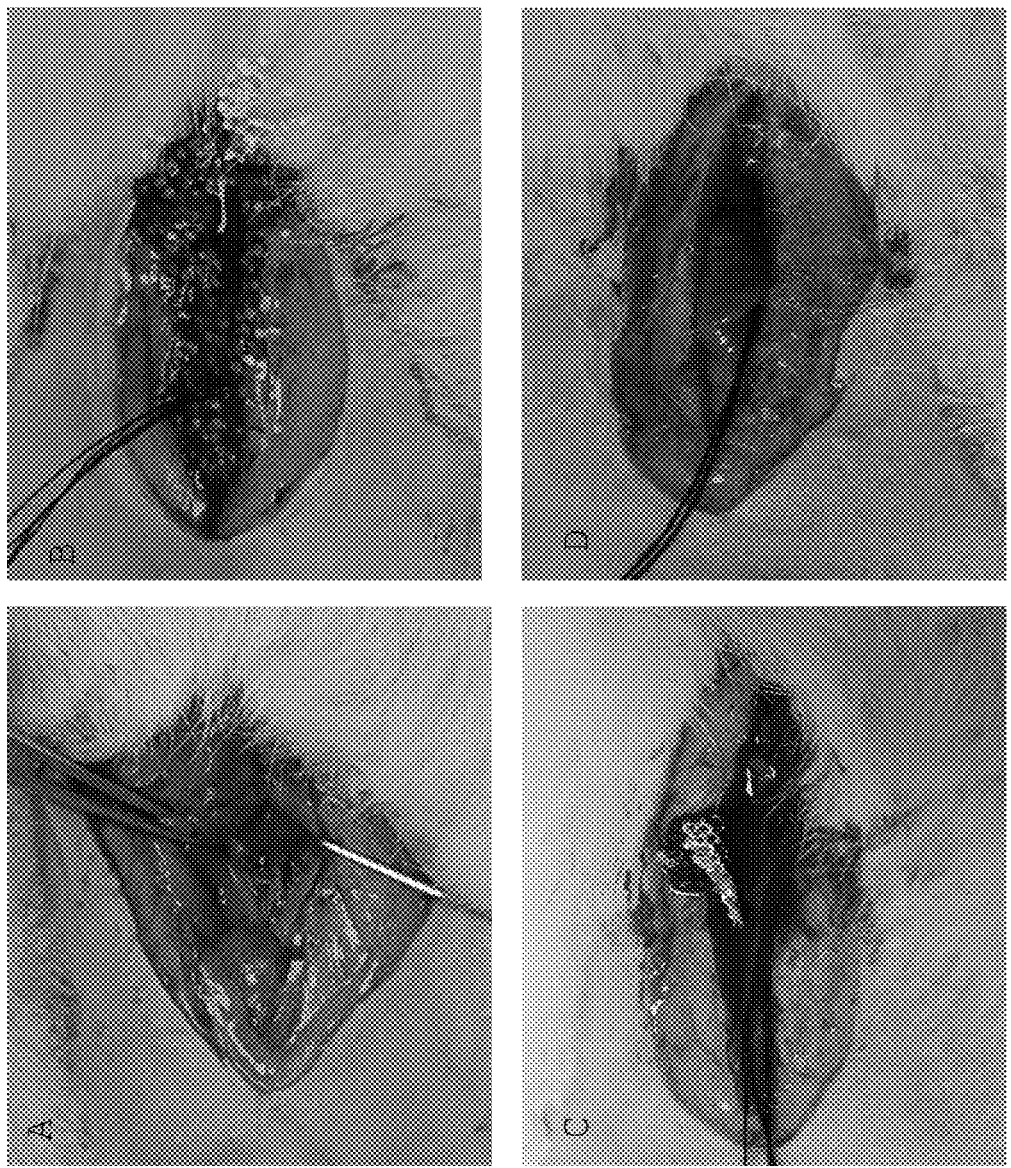
FIG. 5 shows pictures that compare bleeding control between Surgicel™, QuikClot™, and a composition of the present invention. Panel A shows abdominal aortic artery puncture site; Panel B shows the effect of QuikClot™ on bleeding of the aortic artery; Panel C shows the effect of Surgicel™ on bleeding; and Panel D shows the effect of a composition of the present invention on bleeding.

FIG. 5 shows pictures that compare bleeding control between Surgicel™, QuikClot™, and a composition of the present invention. FIG. 5A provides a reference photograph showing the site of artery wounding. As shown in FIG. 5B, when the artery was punctured with a needle and then Quik-Clot™ (2 grams) immediately applied to the injury site, the hemostatic agent failed to arrest bleeding, even after 2 minutes into the procedure, as is evidenced by blood still oozing out of the wound at that time. As shown in FIG. 5C, application of Surgicel™ as the hemostatic agent showed the same pattern, with bleeding continuing more than two minutes after application of the hemostatic agent. In contrast, when a composition of the present invention, produced according to the procedure in Example 3, was used, bleeding was diminished rapidly, and bleeding stopped well within two minutes of application to the wound site (FIG. 5D). Based on this data, it was concluded that the hemostatic agent of the present invention is superior to other agents available in the art, and is capable of arresting bleeding, even heavy arterial bleeds, whereas other hemostatic agents are not capable of doing so.

Figure 6:
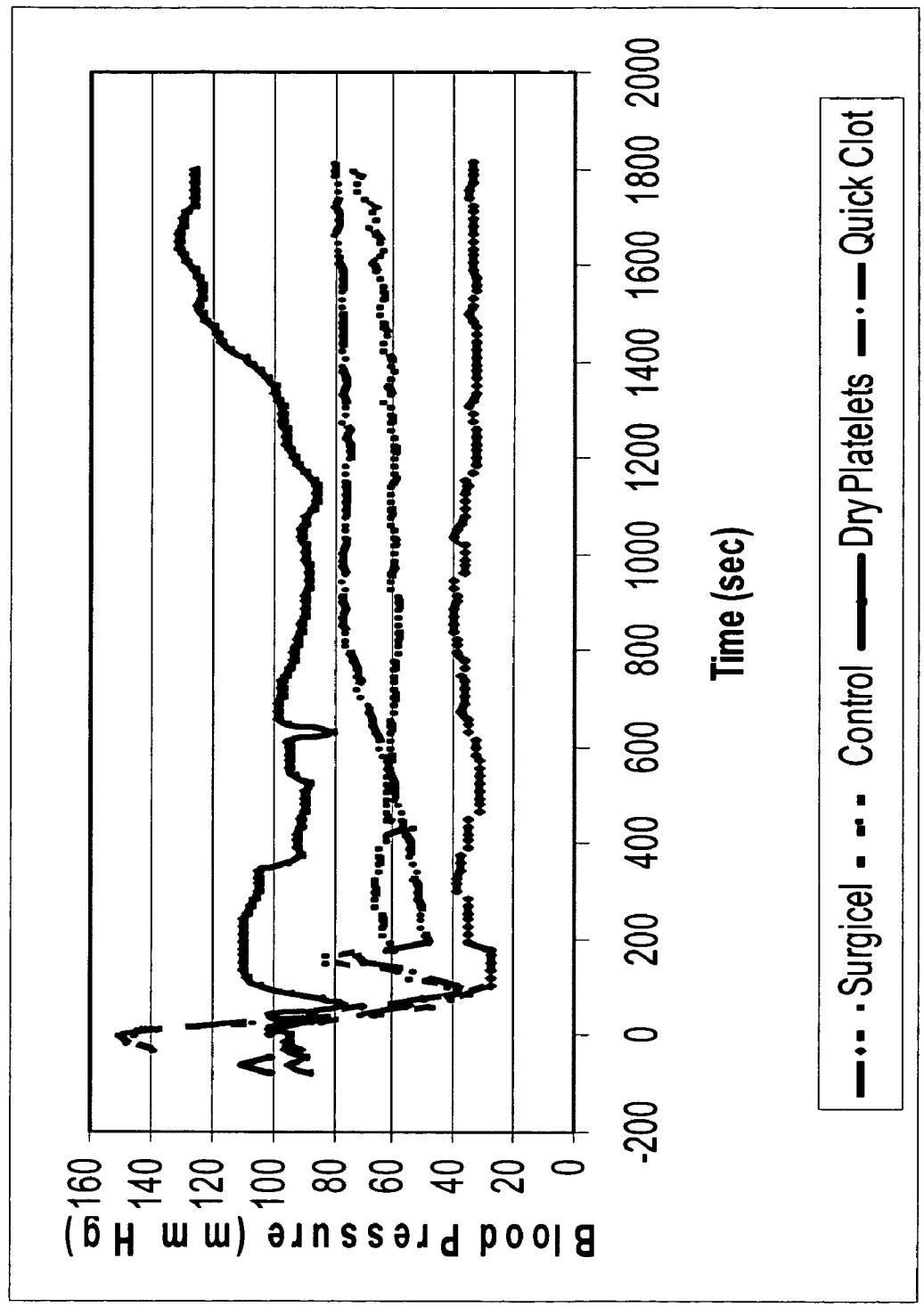
FIG. 6 shows graphs of the blood pressure of rodents having had their abdominal aorta punctured, then treated with freeze-dried platelets of the invention, Surgicel™, QuikClot™, of no hemostat or pressure applied to the bleeding site (control).

To further assay the effects of a composition of the invention in vivo, the vital signs of the rats used in the above experiment were monitored by monitoring the systolic blood pressure, mean blood pressure, and heart-rate over a 30-minute period. FIG. 6 shows a graph of the mean blood pressure of rodents having had their abdominal aorta punctured, then treated with freeze-dried platelets of the invention, Surgicel™, and QuikClot™, with a control (no pressured applied to the bleeding site). Blood pressures were measured using a WECO monitor for 30 minutes. Animals were sacrificed after the procedure.

As shown in FIG. 6, the mean blood pressure of animals in group Surgicel™ and Control (no pressured applied to the bleeding site) never recovered after the puncture procedure. Animals in the QuikClot™ group did regain some pressure, but were not able to return to normal. On the contrary, when treated with a composition of the present invention, normal pressure returned within 1200-1400 seconds after the puncture procedure, and it was stabilized for the duration of the study.

The heart rates of the rodents were monitored and it was found that only in the group treated with the composition of the present invention were heart rates quickly returned to normal (the Control, Surgicel™, and QuikClot™ failed to do so).

The animals were continually visually monitored throughout the procedure. Despite the fact that all animals survived past 30 minutes, the animals in groups Surgicel™, Quik-Clot™, and Control struggled to breath, and had very faint heart rates. In contrast, animals treated with the composition of the present invention were breathing normally with almost normal heart rates. Based on this data, it was concluded that compositions of the invention can be potent in vivo hemostatic agents.

It is clear from the data, that a composition of the invention retained a majority of its physical surface structure and integrity. Furthermore, the composition could participate in collagen remodeling and fibroblast proliferation (see earlier Examples). Without being constrained to any particular theory, it is possible that a natural pool of growth factors could have been contained within the composition, and could aid in wound treatments as well as cell and tissue regeneration.

All of these indications might suggest that the compositions of the invention comprise a unique mixture of platelets and platelet microparticles at a defined ratio. Furthermore, the data also showed that the compositions of the invention were able to quickly seal the high pressure hemorrhaging aortic artery quickly and effectively when applied to it. In addition, this hemostatic activity is superior to QuikClot™ or Surgicel™ and proven to be useful and effective as a hemostatic agent that is capable of stopping bleeding at a high pressure, non-compressible bleeding site.

Example 11

Further Analysis of In Vivo Characteristics

To further assay the properties of a composition made in accordance with Example 2, further in vivo wound healing studies were performed, and analyses of cells from these studies were carried out. For in vivo wound healing studies, diabetic mice (male Lepr db+/+), were used. Thirty animals were ordered and kept five per cage until the wound site was excised. Anesthesia (Nembutal/Pentobarbital) was administered intraperitoneally at a dose of 60 mg/kg. Depth of anesthesia was assessed by pinching the animals' toes and assessing for flexor withdrawal. The back of the anesthetized mouse was shaved using an electric razor. Any remaining traces of hair were removed with hair removal lotion (calcium hydroxide based) applied briefly to the skin and then rinsed with warm saline. Prior to surgery, the shaved skin was cleaned with betadine and then wiped with 70% EtOH. A $1 \times 1$ cm$^2$ full-thickness wound was excised from the hairless dorsum of the mouse, as follows. The skin was lifted using forceps and incised using scissors. Lifting the skin ensured that the incision moved through the panniculus carnosus. Following the first cut, the partially removed skin area was held using forceps and the excision was completed with two or three additional cuts. After completion of excisional wounding, the animals were divided into test groups (ten animals per group), and corresponding test materials were applied on the wound bed. Ten animals received an occlusive dressing only; ten received a single application of $5 \times 10^8$ FDP given on the day of surgery; ten received applications of $5 \times 10^8$ FDP given on the day of surgery and on days 2, 5, 9, and 12 following surgery. Benzoin Tincture Compound was placed around the edges of the wound and Tegaderm was placed to cover the wound. Following the surgery, mice were given Buprenorphine 0.05 mg/Kg$^2$ every 12 hours for 24 hours for post-operative analgesia, and then daily as needed. After complete recovery from anesthesia, mice were transferred to the Animal Core Facility, where they were singularly caged, and then monitored twice a day. Mice were monitored for inactivity, appetite loss, and the wounds were inspected. Wound measurements were taken every other day for the duration of the study. One animal from each group was sacrificed on these days using gas $CO_2$ inhalation. Blood, kidney, and liver samples were harvested from the animals for immunogenic studies and the wound site was removed for immunohistological analysis. Any animals that developed wound infection were excluded from the study.

Figure 7:
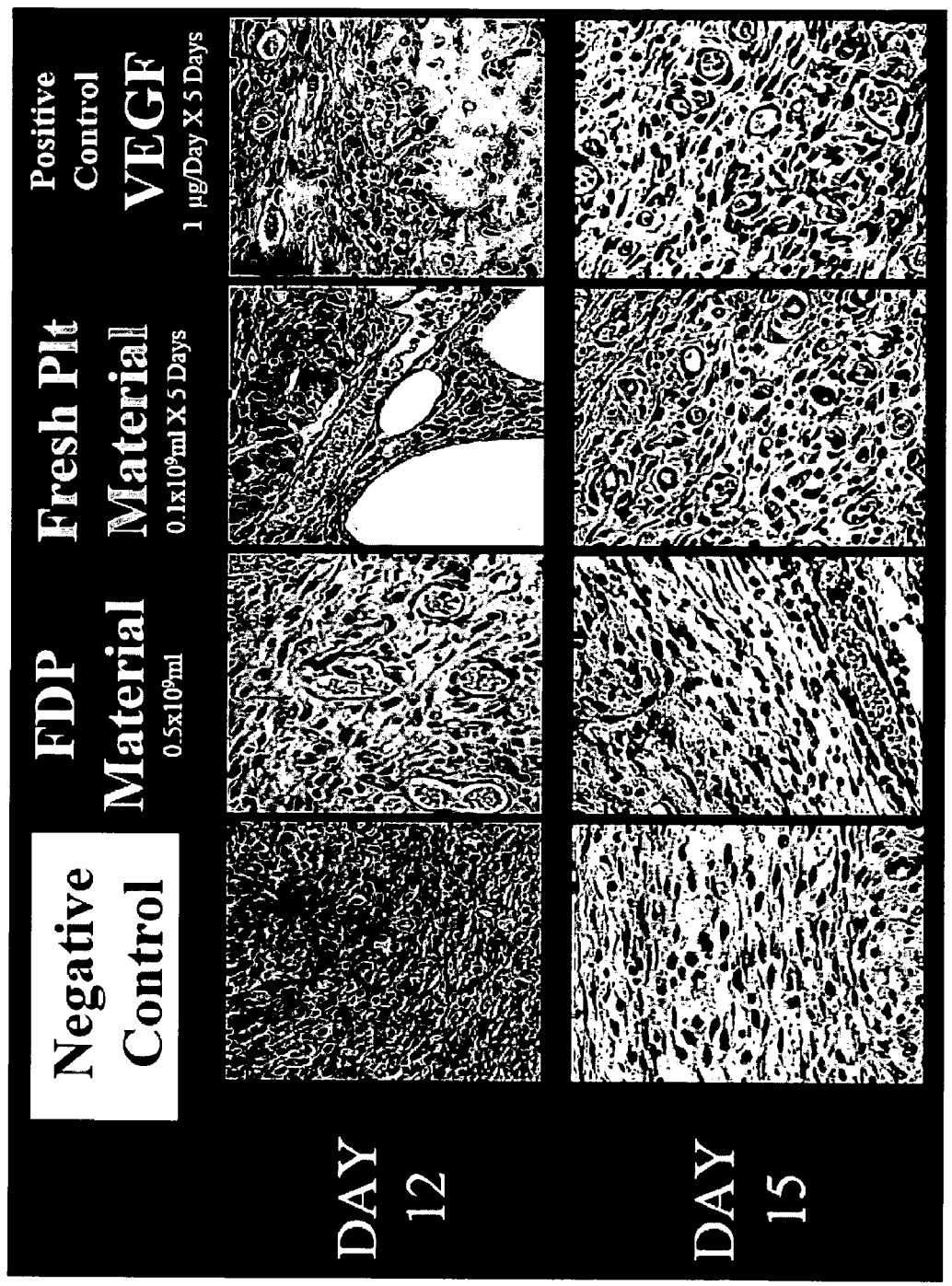
FIG. 7 depicts pictures of microscopic views of the wound beds of wound sites treated with an occlusive dressing, freeze-dried platelets of the invention, or VEGF.

The immunohistological analysis of the wound bed is presented in FIG. 7. The data was developed as follows: The tissue at the wound bed was removed from one animal of each group every third day for staining. Stained sections were scanned at low power to identify areas with the most intense neovascularization. To evaluate neovascularization, 3 fields per slide at 40× magnification were systematically taken, one in the middle of the lesion and two at wound edges.

Careful examination of the wound bed tissue under a microscope revealed that groups that received FDP, fresh platelets, and VEGF underwent intense neovascularization. The newly formed blood vessels can be found at the wound edges as well as in the middle section. When the absolute numbers of blood vessels were counted, the number of blood vessels in the samples that received FDP, fresh platelets, and VEGF were virtually identical. As can be seen in FIG. 7, a microscopic view of the wound bed of the Occlusive Dressing, Single Dose, and Multiple Dose treatment groups at days 1, 9 and 15, shows increased vascularization.

Figure 8:
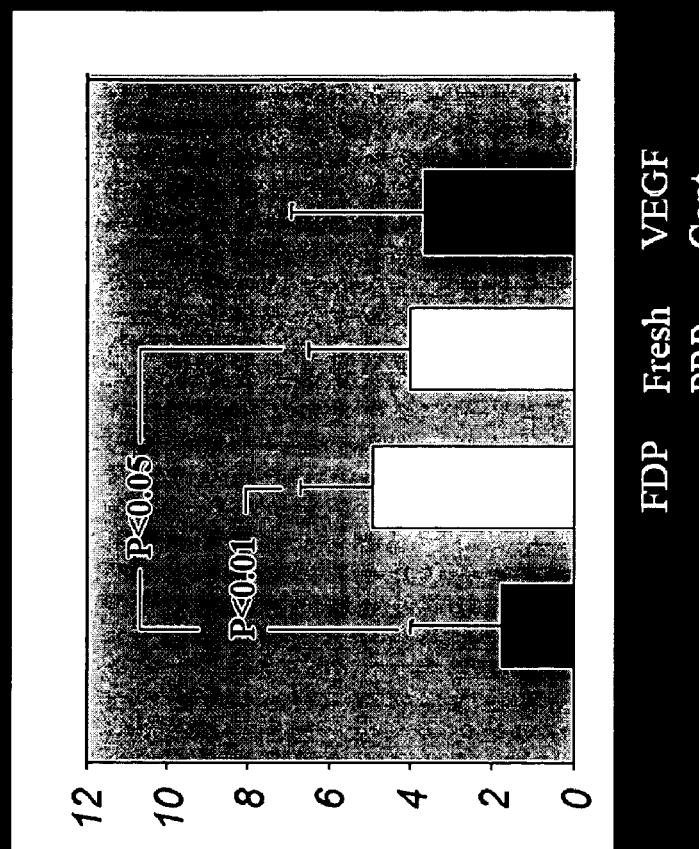
FIG. 8 depicts a graph of quantification of the results of vascularization shown in FIG. 7.

FIG. 8 depicts the data of FIG. 7 graphically. More specifically, FIG. 8 depicts a bar graph quantifying the number of vessels in the wound bed tissue. Because the wound tissues required blood vessels to heal, the application of freeze-dried platelets to the wound bed not only supplied the needed growth factors for tissue regeneration but also stimulated the growth of new blood vessels. This data indicated that the number of blood vessels generated by the composition is similar to that of fresh platelets and VEGF control. Thus, freeze-dried platelets are an effective wound healing agent.

Example 12

Evaluation of Wound Closing Rate and Multiple Dosing

For this Example, a study was conducted to determine the effect of multiple applications of freeze-dried platelets on wound healing compared to animals that received only a 1-time dose on the day of surgery and animals that received an occlusive dressing only. For the Multiple Dose FDP group, animals received 5 applications of $5 \times 10^8$ platelets given on the day of surgery and days 2, 5, 9, and 12 following surgery. For the Single Dose FDP group, animals received a 1-time application of $5 \times 10^8$ platelets given on the day of surgery. Animals in the Occlusive Dressing group did not receive any platelets.

Figure 9:
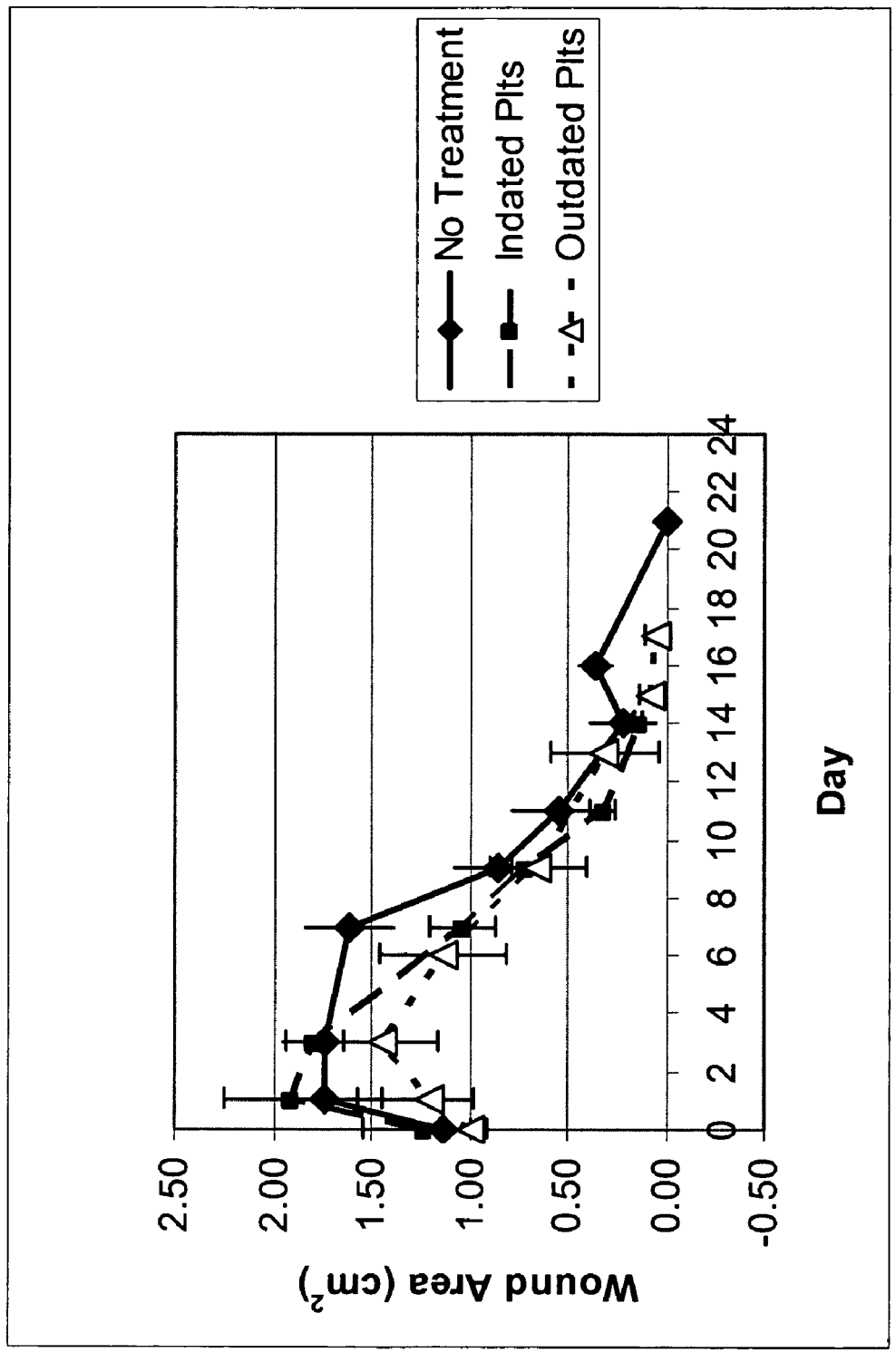
FIG. 9 depicts a graph comparing different treatment regimens in wound healing.

The results of the study are shown in FIG. 9. The Figure shows that animals in the Multiple Dose FDP group demonstrated a much faster rate of wound closure, requiring only 16 days for complete closure. The Single Dose and Occlusive Dressing groups had a much slower rate of wound closure, requiring 17 and 21 days for complete closure. More specifically, wound measurements were taken every other day (or every three days). By day 16, the Multiple Dose group had nearly achieved complete wound closure, while the Single Dose and Occlusive Dressing groups required at least 17 and 21 days, respectively. It is also significant that the Multiple Dose group demonstrated a smaller average wound area than the Single Dose and Occlusive Dressing groups throughout the duration of the study.

Example 13

Evaluation of Wound Closure Rate and Single Dosing Using In-Dated and Out-Dated Platelets To determine the suitability of various types of platelets and platelet preparations for in vivo therapeutic uses, platelets were assayed for their ability to close wounds in single doses. Initially, platelets one day outdated were prepared according to Example 2. Briefly, platelets were collected into acid citrate dextrose (ACD) anticoagulant buffer (1.5 volumes+8.5 volumes blood). Platelet Rich Plasma (PRP) was obtained by low speed centrifugation 135×g for 15 minutes to remove red blood cells. The PRP was acidified to pH 6.5 by adding $\frac{1}{14}$ volumes of ACD and then pelleted by centrifuge at 1000×g for 10 minutes. The platelet pellet was resuspended in 1 ml of Cation-Free Tyrodes Buffer containing 50 mM Trehalose, pH 6.8 and adjusted to $\sim 1 \times 10^9$ platelets/ml. The mixture was incubated for 2 hours at 37° C., mixing once each half hour. Finally, the albumin concentration was adjusted to 5% of platelet preparation for lyophilization.

Figure 10:
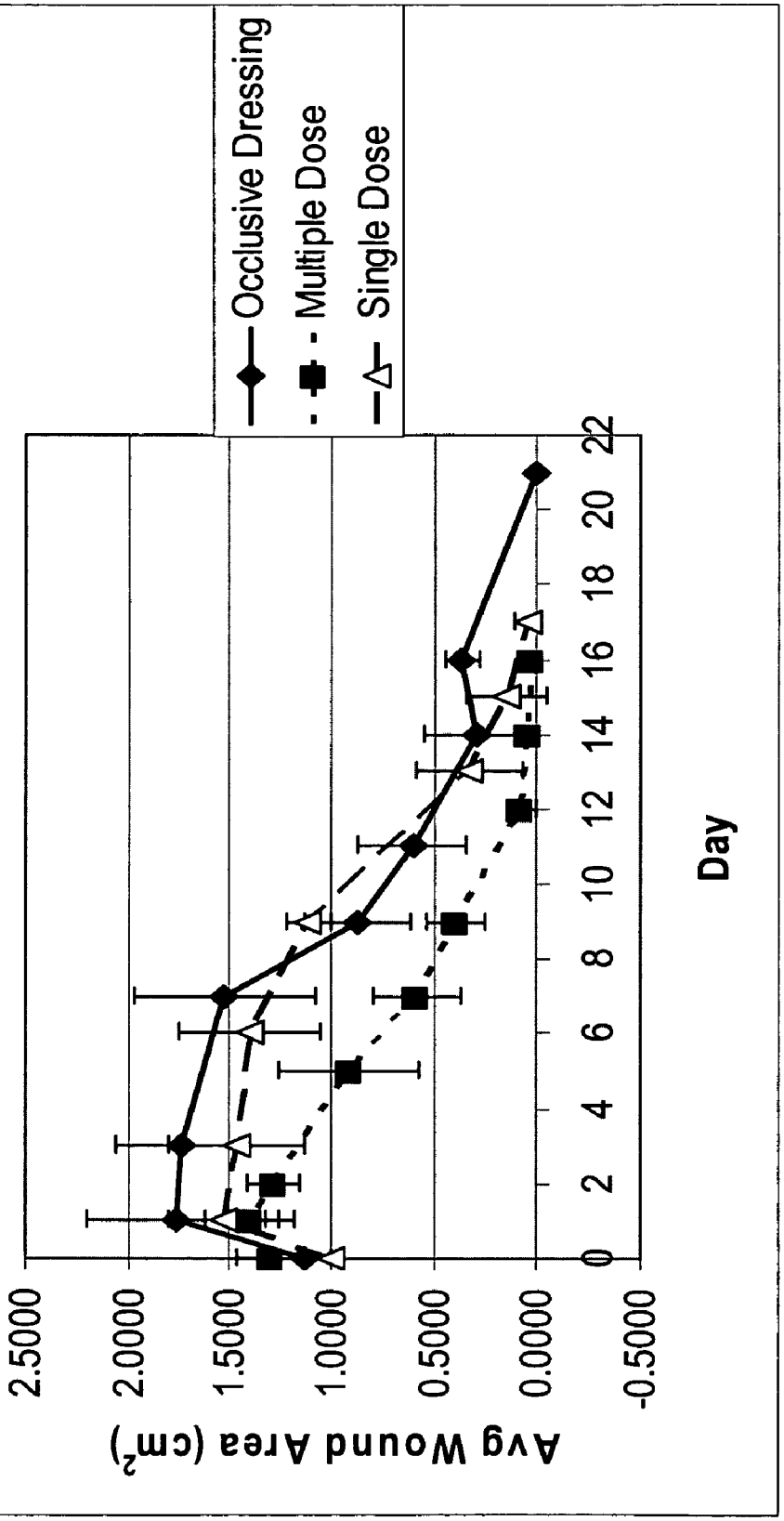
FIG. 10 depicts a graph comparing the effectiveness in treating wounds of in-dated and out-dated platelets as sources for freeze-dried platelets.

For the study, the effect of a single dose application to animals of either in-dated or out-dated FDP on wound healing was compared to the effect of an occlusive dressing only. For the FDP group, animals received one application of $5 \times 10^8$ platelets given on the day of surgery. Animals in the Occlusive Dressing group did not receive any platelets. Wound measurements were taken every other day (or every three days). As can be seen from FIG. 10, single doses of either in-dated or out-dated freeze dried platelets of the invention required 17 days to completely heal the wound. In contrast, and in agreement with the results presented above, Occlusive Dressing groups required 21 days to completely heal the wounds. Thus, there is no difference in wound healing capability between in-dated and out-dated platelets, and both are superior to occlusive dressing techniques.

Example 14

A Delivery System for Compositions of the Invention

A composition according to the invention was formulated to be suspended in compressed air for use in an aerosol system. In this system, the compressed air acted as a propellant to force the platelet composition onto a site of bleeding. In the system, the air pushed down on the composition, forcing the composition through the dip tube of the aerosol system and through a valve when opened. The spray device contained a nozzle that inserted into the abdominal cavity through the wound site. The resulting spray, which contained a composition of the invention, acted on the bleed site to stop bleeding.

REFERENCES CITED

Christenson, J T, A Kalangos, 2004, Autologous fibrin glue reinforced by platelets in surgery of ascending aorta*: Thorac. Cardiovasc. Surg., v. 52, p. 225-229.

Gilbert, G E, P J Sims, T Wiedmer, B Furie, B C Furie, S J Shattil, 1991, Platelet-derived microparticles express high affinity receptors for factor VIII: J. Biol. Chem., v. 266, p. 17261-17268.

Hoffman, M, D M Monroe, H R Roberts, 1992, Coagulation factor IXa binding to activated platelets and platelet-derived microparticles: a flow cytometric study: Thromb. Haemost., v. 68, p. 74-78.

Holme, P A, F Brosstad, N O Solum, 1995, Platelet-derived microvesicles and activated platelets express factor Xa activity: Blood Coagul. Fibrinolysis, v. 6, p. 302-310.

Mazzucco, L, D Medici, M Serra, R Panizza, G Rivara, S Orecchia, R Libener, E Cattana, A Levis, P G Betta, P Borzini, 2004, The use of autologous platelet gel to treat difficult-to-heal wounds: a pilot study: Transfusion, v. 44, p. 1013-1018.

Nieuwland, R, R J Berckmans, R C Rotteveel-Eijkman, K N Maquelin, K J Roozendaal, P G Jansen, K ten Have, L Eijsman, C E Hack, A Sturk, 1997, Cell-derived microparticles generated in patients during cardiopulmonary bypass are highly procoagulant: Circulation, v. 96, p. 3534-3541.

Oikarinen, K S, G K Sandor, V T Kainulainen, M Salonen-Kemppi, 2003, Augmentation of the narrow traumatized anterior alveolar ridge to facilitate dental implant placement: Dent. Traumatol., v. 19, p. 19-29.

Pierce, G F, T A Mustoe, J Lingelbach, V R Masakowski, G L Griffin, R M Senior, T F Deuel, 1989, Platelet-derived growth factor and transforming growth factor-beta enhance tissue repair activities by unique mechanisms: J. Cell Biol., v. 109, p. 429-440.

Prior, J J, D G Wallace, A Hamer, N Powers, 1999, A sprayable hemostat containing fibrillar collagen, bovine thrombin, and autologous plasma: Ann. Thorac. Surg., v. 68, p. 479-485.

Rosing, J, E M Bevers, P Comfurius, H C Hemker, G van Dieijen, H J Weiss, R F Zwaal, 1985, Impaired factor X and prothrombin activation associated with decreased phospholipid exposure in platelets from a patient with a bleeding disorder: Blood, v. 65, p. 1557-1561.

Serebruany, V L, J V Ordonez, V V Yurovsky, P A Gurbel, 1998, Crossreactivity of Human versus Swine Platelet Surface Antigens Is Similar for Glycoproteins Ib and IIIa, but Not for the Glycoprotein IIb/IIIa Complex: J. Thromb. Thrombolysis., v. 5, p. 37-41.

Sims, P J, E M Faioni, T Wiedmer, S J Shattil, 1988, Complement proteins C5b-9 cause release of membrane vesicles from the platelet surface that are enriched in the membrane receptor for coagulation factor Va and express prothrombinase activity: J. Biol. Chem., v. 263, p. 18205-18212.

Sims, P J, S A Rollins, T Wiedmer, 1989, Regulatory control of complement on blood platelets. Modulation of platelet procoagulant responses by a membrane inhibitor of the C5b-9 complex: J. Biol. Chem., v. 264, p. 19228-19235.

Steed, D L, 1997, The role of growth factors in wound healing: Surg. Clin. North Am., v. 77, p. 575-586.

Tans, G, J Rosing, M C Thomassen, M J Heeb, R F Zwaal, J H Griffin, 1991, Comparison of anticoagulant and procoagulant activities of stimulated platelets and platelet-derived microparticles: Blood, v. 77, p. 2641-2648.

Wajon, P, J Gibson, R Calcroft, C Hughes, B Thrift, 2001, Intraoperative plateletpheresis and autologous platelet gel do not reduce chest tube drainage or allogeneic blood transfusion after reoperative coronary artery bypass graft: Anesth. Analg., v. 93, p. 536-542.

All references cited herein are incorporated herein by reference in their entireties.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method of treating bleeding in a subject suffering from bleeding, said method comprising administering a composition comprising freeze-dried platelets to the subject, wherein the amount of platelets administered to the subject is sufficient to treat the bleeding, and wherein the freeze-dried platelets are produced by a process consisting essentially of:
obtaining platelet rich plasma,
adding acid citrate dextrose to obtain a pH of about 6.8 in the platelet rich plasma,
centrifuging the platelet rich plasma to obtain a platelet pellet and platelet poor plasma,
isolating the platelet pellet from the platelet poor plasma,
suspending the isolated platelet pellet in a divalent cation free buffer comprising about 5.0 mM glucose, about 50 mM trehalose at about pH 6.8,
incubating the suspension for about 2 hours at about 37° C.,
adding albumin or Ficoll® to the suspension to a final concentration of about 5% w/v,
lyophilizing the suspension without immersing the suspension in liquid nitrogen, and
wherein the process does not include contacting the platelets with a platelet inhibitor.

2. The method of claim 1, wherein said administering comprises applying freeze-dried platelets or a composition comprising freeze-dried platelets directly to the site of bleeding.

3. The method of claim 1, wherein the bleeding is from a high-pressure artery.

4. The method of claim 1, further comprising rehydrating the freeze-dried platelets before administering them.

5. The method of claim 1, wherein said administering comprises injecting or infusing freeze-dried platelets or a composition comprising freeze-dried platelets into the blood system of the subject.

6. The method of claim 5, further comprising rehydrating the freeze-dried platelets before administering them.

7. The method of claim 1, wherein the method is a method of treating acute bleeding.

8. The method of claim 7, wherein the bleeding is due to a wound or trauma.

9. The method of claim 1, wherein the method is a method of treating a bleeding disorder.

10. The method of claim 9, wherein the bleeding disorder is hemophilia.

11. The method of claim 9, wherein the bleeding disorder is a side-effect of a treatment regimen for a disease or disorder other than a bleeding disease or disorder.

12. The method of claim 11, wherein the bleeding disorder is a side-effect of an anti-cancer treatment.

13. The method of claim 1, wherein the bleeding is due to surgery.

* * * * *